(12) United States Patent
Menke et al.

(10) Patent No.: US 6,432,880 B1
(45) Date of Patent: Aug. 13, 2002

(54) SUBSTITUTED 2-PHENYLPYRIDINES AS HERBICIDES

(75) Inventors: Olaf Menke, Altleiningen; Markus Menges, Bensheim; Ingo Sagasser, Eppelheim; Gerhard Hamprecht, Weinheim; Robert Reinhard; Cyrill Zagar, both of Ludwigshafen; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/869,840

(22) PCT Filed: Jan. 8, 2000

(86) PCT No.: PCT/EP00/00095

§ 371 (c)(1),
(2), (4) Date: Jul. 5, 2001

(87) PCT Pub. No.: WO00/42015

PCT Pub. Date: Jul. 20, 2000

(30) Foreign Application Priority Data

Jan. 15, 1999 (DE) .......................... 199 01 259

(51) Int. Cl.[7] .................. A01N 43/40; C07D 213/30
(52) U.S. Cl. .................. 504/254; 546/295; 546/280.4; 546/280.1
(58) Field of Search .............. 546/295, 280.4, 546/280.1; 504/254

(56) References Cited

U.S. PATENT DOCUMENTS 5,529,976 A  6/1996  Kehne ................ 504/213
5,747,422 A  5/1998  Schaefer ............. 504/244
5,958,837 A  9/1999  Schaefer ............. 504/244

FOREIGN PATENT DOCUMENTS

WO   96/21646   7/1996
WO   96/21647   7/1996
WO   98/07700   2/1998

OTHER PUBLICATIONS

CA 125:143104, Godard et al. 1996.*
CA 83:9802, Headford et al. 1975.*

* cited by examiner

*Primary Examiner*—Jane Fan
(74) *Attorney, Agent, or Firm*—Keil & Weinkauf

(57) ABSTRACT

2-Phenylpyridines I

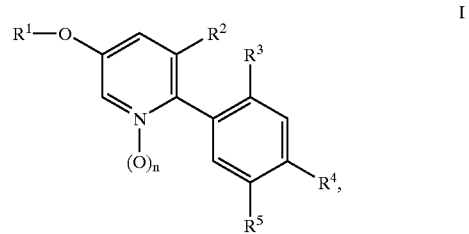

an their salts, wherein $R^1$ to $R_{17}$, $X_1$–$X_3$ are as defined in the specification. The compounds are useful as herbicides, desiccants and defoliants.

10 Claims, No Drawings

SUBSTITUTED 2-PHENYLPYRIDINES AS HERBICIDES

This application is a 371 of PCT/EP00/00095 filed Jan. 8, 2000 now WO 00/42015 filed Jul. 20, 2000.

The present invention relates to novel substituted 2-phenyl-5 pyridines of the formula I

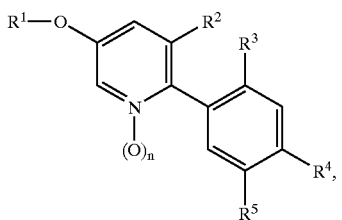

where:

n is zero or 1;

$R^1$ is aminosulfonyl, $C_1$–$C_6$-alkylsulfinyl, $C_1$–$C_6$-alkylsulfonyl or $C_1$–$C_6$-haloalkylsulfonyl;

$R^2$,$R^3$ independently of one another are hydrogen or halogen;

$R^4$ is cyano, hydroxyl, halogen, $C_1$–$C_6$-alkoxy or phenylmethoxy, where the phenyl ring may be unsubstituted or may carry from one to three substituents, in each case selected from the group consisting of hydroxyl, halogen, $C_1$–$C_6$-alkyl, $C_1$–$C_6$-haloalkyl, $C_1$–$C_6$-alkoxy, $C_1$–$C_6$-haloalkoxy, hydroxycarbonyl, ($C_1$–$C_6$-alkoxy)carbonyl and ($C_1$–$C_6$-alkoxy)carbonyl-$C_1$–$C_6$-alkoxy;

$R^5$ is hydrogen, nitro, cyano, hydroxyamino, halogen, $C_1$–$C_6$-alkyl, $C_1$–$C_6$-haloalkyl, —COCl, —CO—$OR^6$, —CO—N($R^7$)$R^8$, —CO—O—($C_1$–$C_4$-alkylene)—CO—$OR^6$, —CO—O—($C_1$–$C_4$-alkylene)—CO—N($R^7$)$R^8$, —$X^1$—($C_1$–$C_4$-alkylene)—CO—$OR^6$, —$X^1$—($C_1$–$C_4$-alkylene)—CO—$OR^6$, —$X^1$—($C_1$–$C_4$-alkylene)—CO—O—($C_1$–$C_4$-alkylene)—CO—$OR^6$, —$X^1$—($C_1$–$C_4$-alkylene)—CO—N($R^7$)$R^8$, —$X^1$—$R^9$, —CH=C($R^{10}$)—CO—$OR^6$, —CH=C($R^{10}$)—CO—O—($C_1$–$C_4$-alkylene)—CO—$OR^6$, —CH=C($R^{10}$)—CO—N($R^7$)$R^8$, formyl, —CO—$R^6$,

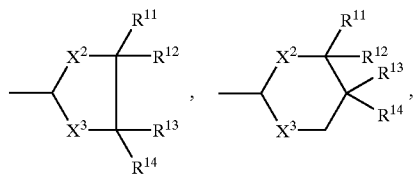

—C($R^8$)=N—$OR^{15}$, —$X^1$—($C_1$–$C_4$-alkylene)—C($R^8$)=N—$OR^{15}$, —CH=C($R^{10}$)—C($R^8$)=N—$OR^{15}$, —CH($C_1$–$C_6$-alkoxy)$_2$, —CN($R^{16}$)$R^{17}$, —N($R^{16}$)—SO$_2$—($C_1$–$C_6$-alkyl), —N($R^{16}$)—CO—($C_1$–$C_6$-alkyl), chlorosulfonyl, hydroxysulfonyl or —SO$_2$—N($R^{18}$)$R^{19}$;

$R^6$ is hydrogen, $C_1$–$C_6$-alkyl, $C_1$–$C_6$-haloalkyl, $C_3$–$C_6$-alkenyl, $C_3$–$C_6$-alkynyl, $C_3$–$C_6$-cycloalkyl or $C_1$–$C_6$-alkoxy-$C_1$–$C_6$-alkyl;

$R^7$ is hydrogen or $C_1$–$C_6$-alkyl;

$R^8$ is hydrogen, hydroxyl, $C_1$–$C_6$-alkyl, hydroxycarbonyl-$C_1$–$C_6$-alkyl, ($C_1$–$C_6$-alkoxy)carbonyl-$C_1$–$C_6$-alkyl, $C_1$–$C_6$-alkoxy, $C_1$–$C_6$-haloalkoxy, phenyl-$C_1$–$C_6$-alkoxy, $C_3$–$C_6$-alkenyloxy or $C_3$–$C_6$-alkynyloxy;

$R^9$ is hydrogen, $C_1$–$C_6$-alkyl, $C_1$–$C_6$-haloalkyl, $C_3$–$C_6$-alkenyl, $C_3$–$C_6$-alkynyl, $C_3$–$C_6$-cycloalkyl or $C_1$–$C_6$-alkoxy-$C_1$–$C_6$-alkyl;

$R^{10}$ is hydrogen, halogen or $C_1$–$C_6$-alkyl;

$R^{11}$–$R^{14}$ independently of one another are hydrogen, $C_1$–$C_6$-alkyl or ($C_1$–$C_6$-alkoxy)carbonyl;

$R^{15}$ is hydrogen, $C_1$–$C_6$-alkyl, phenyl-$C_1$–$C_6$-alkyl, ($C_1$–$C_6$-alkoxy)carbonyl-$C_1$–$C_6$-alkyl, $C_3$–$C_6$-alkenyl or $C_3$–$C_6$-alkynyl;

$R^{16}$ is hydrogen or $C_1$–$C_6$-alkyl;

$R^{17}$ is hydrogen, $C_1$–$C_6$-alkyl, hydroxycarbonyl-$C_1$–$C_6$-alkyl, ($C_1$–$C_6$-alkoxy)carbonyl-$C_1$–$C_6$-alkyl or $C_1$–$C_6$-alkoxy;

$R^{18}$ is hydrogen or $C_1$–$C_6$-alkyl;

$R^{19}$ is hydrogen, $C_1$–$C_6$-alkyl, hydroxycarbonyl-$C_1$–$C_6$-alkyl, ($C_1$–$C_6$-alkoxy)carbonyl-$C_1$–$C_6$-alkyl or $C_1$–$C_6$-alkoxy;

$X^1$–$X^3$ independently of one another are oxygen or sulfur; and the agriculturally useful salts of the compounds I where $R^6$=hydrogen.

Moreover, the invention relates to the use of the compounds I as herbicides or for the desiccation/defoliation of plants, herbicidal compositions and compositions for the desiccation and/or defoliation of plants which comprise the compounds I as active ingredients, methods for controlling undesirable vegetation and for the desiccation and/or defoliation of plants using the compounds I, processes for preparing the compounds I and herbicidal compositions and compositions for the desiccation and/or defoliation of plants using the compounds I and also intermediates of the formula IIa.

WO 96/21646 and WO 96/21647 have already described certain substituted 2-phenylpyridines of the type of the compounds I having, inter alia, $C_1$–$C_4$-alkylsulfinyl or $C_1$–$C_4$-alkylsulfonyl in the 5-position of the pyridine ring for use as herbicides and desiccants/defoliants.

Furthermore, 2-phenylpyridines having herbicidal and/or desiccant/defoliant activity, which differ from the present compounds I in that $R^1$ is directly attached to the pyridine ring, form part of the subject matter of WO 98/07700.

However, the herbicidal activity of the prior art compounds is, with a view to the harmful plants, not always entirely satisfactory.

It is an object of the present invention, therefore, to provide novel herbicidally active compounds which allow better selective control of undesirable plants than known compounds. It is a further object to provide novel compounds which have a desiccant/defoliant action.

We have found that these objects are achieved by the herbicidal substituted 2-phenylpyridines of the formula I defined at the outset and by novel intermediates IIa for their preparation.

Furthermore, we have found herbicidal compositions which comprise the compounds I and have very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oilseed rape, sunflower, soybean or field beans, in particular cotton and potatoes. In this regard, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. The invention provides both the pure enantiomers or diastereomers and mixtures thereof.

The substituted 2-phenylpyridines I where $R^6$=hydrogen may be present in the form of their agriculturally useful salt, the type of salt being generally immaterial. In general, the salts of such bases are suitable where the herbicidal activity is not adversely affected in comparison to the free compound I.

Suitable salts are, in particular, those of the alkali metals, preferably sodium and potassium salts, the alkaline earth metals, preferably calcium and magnesium salts, those of the transition metals, preferably zinc and iron salts, and also ammonium salts, where the ammonium ion may, if desired, carry one to four $C_1$–$C_4$-alkyl, hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)ammonium salts, furthermore phosphonium salts, sulfonium salts, such as, preferably, tri-($C_1$–$C_4$-alkyl)sulfonium salts, and sulfoxonium salts, such as, preferably, tri-($C_1$–$C_4$-alkyl)sulfoxonium salts.

The organic molecular moieties mentioned for the substituents $R^1$ and $R^4$ to $R^{19}$ or as radicals on a phenyl ring are collective terms for individual listings of the individual group members. All hydrocarbon chains, i.e. all alkyl, haloalkyl, phenylalkyl, alkylene, alkoxy, haloalkoxy, phenylalkoxy, alkylsulfinyl, alkylsulfonyl, hydroxycarbonylalkyl, alkenyl, alkynyl, alkenyloxy and alkynyloxy moieties can be straight-chain or branched. Halogenated substituents preferably carry one to five identical or different halogen atoms.

The term halogen represents in each case fluorine, chlorine, bromine or iodine, in particular fluorine or chlorine.

Examples of other meanings are:

$C_1$–$C_6$-alkyl: $C_1$–$C_4$-alkyl such as $CH_3$, $C_2H_5$, $CH_2$-$C_2H_5$, $CH(CH_3)_2$, n-butyl, $CH(CH_3)$—$C_2H_5$, $CH_2$—$CH(CH_3)_2$ and $C(CH_3)_3$, or, for example, n-pentyl, 1-methylbutyl, 2-methylbutyl, 3-methylbutyl, 2,2-dimethyipropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, $CH_2$—$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e., for example, $CH_2F$, $CHF_2$, $CF_3$, $CH_2Cl$, $CH(Cl)_2$, $C(Cl)_3$, $CHFCl$, $CF(Cl)_2$, $CF_2Cl$, $CF_2Br$, 1-fluoroethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 1,2-dichloroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, 5,5,5-trichloropentyl, undecafluoropentyl, 6-fluorohexyl, 6-chlorohexyl, 6-bromohexyl, 6-iodohexyl, 6,6,6-trichlorohexyl or dodecafluorohexyl, in particular $CH_2F$, $CHF_2$, $CF_3$, $CH_2Cl_2$-fluoroethyl, 2-chloroethyl, 1,2-dichloroethyl, 2,2,2-trifluoroethyl or $C_2F_5$;

Phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)eth-1-yl, 1-(benzyl)-1-(methyl)eth-1-yl, 1-(benzyl)prop-1-yl or 2-phenylhex-6-yl, in particular benzyl or 2-phenylethyl;

$C_3$–$C_6$-cycloalkyl: cyclopropyl, cyclobutyl, cyclopentyl or cyclohexyl, in particular cyclopentyl or cyclohexyl;

$C_1$–$C_4$-alkylene: —$CH_2$—, —$CH(CH_3)$—, 1,2-ethylene, 1,1-propylene, 1,2-propylene, 1,3-propylene, —CC$(CH_3)_2$—, 1,1-butylene, 1,2-butylene, 1,3-butylene, 1,4-butylene, 2,2-butylene, 2,3-butylene, 2-methyl-1,1-propylene, 2-methyl-1,2-propylene or 2-methyl-1,3-propylene, preferably methylene, 1,1-ethylene, 1,2-ethylene, 1,1-propylene or 2,2-propylene;

$C_1$–$C_6$-alkoxy: for example $OCH_3$, $OC_2H_5$, n-propoxy, $OCH(CH_3)_2$, n-butoxy, $OCH(CH_3)$—$C_2H_5$, $OCH_2$–CH$(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular $OCH_3$, $OC_2H_5$, $OCH(CH_3)_2$ or $OC(CH_3)_3$;

$C_1$–$C_6$-haloalkoxy: $C_1$–$C_6$-alkoxy as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, $OCHFC_1$, $OCF(Cl)_2$, $OCF_2Cl$, $OCF_2Br$, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, $OCF_2$—$C_2F_5$, 1—($CH_2F$)-2-fluoroethoxy, 1—($CH_2Cl$)-2-chloroethoxy, 1—($CH_2Br$)-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, undecafluoropentoxy, 6-fluorohexoxy, 6-chlbrohexoxy, 6-bromohexoxy or dodecafluorohexoxy;

Phenyl-$C_1$–$C_6$-alkoxy: for example benzyloxy, 1-phenylethoxy, 2-phenylethoxy, 1-phenylprop-1- yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 4-phenylbut-2-yloxy, 1-(benzyl)eth-1-yloxy, 1-(benzyl)$_1$-(methyl)eth-1-yloxy, 1-(benzyl)prop-1-yloxy or 2-phenylhex-6-yloxy, in particular benzyloxy or 2-phenylethoxy;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, $CH_2OCH_3$, $CH_2OC_2H_5$, $CH_2OCH_2$—$C_2H_5$, $CH_2OCH(CH_3)_2$, $CH_2OCH_2CH_5$, (1-methylpropoxy)methyl, (2-methylpropoxy)methyl, $CH_2OC(CH_3)_3$, $CH_2O(CH_2)_3$—$C_2H_5$, $CH_2O(CH_2)_4$—$C_2H_5$, $CH(CH_3)OCH_3$, $CH(CH_3)OC_2H_5$, $CH_2CH_2OCH_3$, $CH_2CH_2OC_2H_5$, $CH_2CH_2OCH_2$—$C_2H_5$, $CH_2CH_2OH(CH_3)_2$, $CH_2CH_2OCH_2CH_2$—$C_2H_5$, 2-(1-methylpropoxy)ethyl, 2-(2-methylpropoxy)ethyl, $CH_2CH_2OC(CH_3)_3$, $CH_2CH_2O(CH_2)_3$—$C_2H_5$, $CH_2CH_2O(CH_2)_4$—$C_2H_5$, 2-($OCH_3$)propyl, 2-($OC_2H_5$)propyl, 2-($OCH_2$—$C_2H_5$)propyl, 2-[$OCH(CH_3)_2$]propyl, 2-($OCH_2CH_2$—$C_2H_5$)propyl, 2-(1-methylpropoxy)propyl, 2-(2-methylpropoxy)propyl, 2-[$OC(CH_3)_3$]propyl, 3-($OCH_3$)propyl, 3-($OC_2H_5$)propyl, 3-($OCH_2$—$C_2H_5$)propyl, 3-[$OCH(CH_3)_2$]propyl, 3-($OCH_2CH_2$—$C_2H_5$)propyl, 3-(1-methylpropoxy)propyl, 3-(2-methylpropoxy)propyl, 3-[$OC(CH_3)_3$]propyl, 3-[$O(CH_2)_3$—$C_2H_5$]propyl, 3-[$O(CH_2)_4$—$C_2H_5$]propyl, 2-($OCH_3$)butyl, 2-($OC_2H_5$)butyl, 2-($OCH_2$—$C_2H_5$)butyl, 2-[$OCH(CH_3)_2$]butyl, 2-($OCH_2CH_2$—$C_2H_5$)butyl, 2-(1-methylpropoxy)butyl, 2-(2-methylpropoxy)butyl, 2-[$OC(CH_3)_3$]butyl, 3-($OCH_3$)butyl, 3-($OC_2H_5$)butyl, 3-($OCH_2$—$C_2H_5$)butyl, 3-[$OCH(CH_3)_2$]butyl, 3-($OCH_2CH_2$—$C_2H_5$)butyl, 3-(1-methylpropoxy)butyl, 3-(2-methylpropoxy)butyl, 3-[$OC(CH_3)_3$]butyl, 4-($OCH_3$)butyl, 4-($OC_2H_5$)butyl, 4-($OCH_2$—$C_2H_5$)butyl, 4-[$OCH(CH_3)_2$]butyl, 4-($OCH_2CH_2$—$C_2H_5$)butyl, 4-(1-methylpropoxy)butyl, 4-(2-methylpropoxy)butyl, 4-[$OC(CH_3)_3$]butyl, 4-[$O(CH_2)_3$—$C_2H_5$]butyl, 4-[$O(CH_2)_4$—$C_2H_5$]butyl, 5-($OCH_3$)pentyl, 5-($OC_2H_5$)pentyl, 5-($OCH_2$—$C_2H_5$)pentyl, 5-[$OCH(CH_3)_2$]pentyl, 5-($OCH_2CH_2$—$C_2H_5$)pentyl, 5-(1-methylpropoxy)pentyl, 5-(2-methylpropoxy)pentyl, 5-[$OC(CH_3)_3$]pentyl, 5-[$O(CH_2)_3$—$C_2H_5$]pentyl, 5-[$O(CH_2)_4$—$C_2H_5$]pentyl, 6-($OCH_3$)hexyl, 6-($OC_2H_5$)hexyl, 6-($OCH_2$—$C_2H_5$)hexyl, 6-[$OCH(CH_3)_2$]hexyl, 6-($OCH_2CH_2$—$C_2H_5$)hexyl, 6-(1-Methylpropoxy)hexyl, 6-(2-methylpropoxy)hexyl, 6-[$OC(CH_3)_3$]hexyl, 6-[$O(CH_2)_3$—$C_2H_5$]hexyl or 6-[$O(CH_2)_4$—$C_2H_5$]hexyl, in particular $CH_2OCH_3$, $CH(CH_3)OCH_3$, $CH_3CH_2OCH_3$ or $CH(CH_3)CH_2OCH_3$;

Hydroxycarbonyl-$C_1$–$C_6$-alkyl: for example $CH_2COOH$, $CH(CH_3)COOH$, $CH_2CH_2COOH$, 1-(COOH)prop-1-yl, 2-(COOH)prop-1-yl, 3-(COOH)prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)eth-1-yl, 1-($CH_2COOH$)prop-1-yl, 5-(COOH)pent-1-yl or 6-(COOH)hex-1-yl;

($C_1$–$C_6$-alkoxy)carbonyl: $COOCH_3$, $COOC_2H_5$, n-propoxycarbonyl, $OCH(CH_3)_2$, n-butoxycarbonyl, 1-methylpropoxycarbonyl, 2-methylpropoxycarbonyl, $OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-$C_2H_5$-1-$CH_3$-propoxycarbonyl or 1-$C_2H_5$-2-$CH_3$-propoxycarbonyl, in particular $COOCH_3$, $COOC_2H_5$ or $COOC(CH_3)_3$;

($C_1$–$C_6$-alkoxy)carbonyl-$C_1$–$C_6$-alkyl: $C_1$–$C_6$-alkyl which is substituted by ($C_1$–$C_6$-alkoxy)carbonyl as mentioned above, i.e., for example, $CH_2COOCH_3$, $CH_2COOC_2H_5$, $CH_2COOCH_2$—$C_2H_5$, $CH_2COOCH(CH_3)_2$, $CH_2COOCH_2CH_2$—$C_2H_5$, (1-methylpropoxycarbonyl)methyl, (2-methylpropoxycarbonyl)methyl, $CH_2COOC(CH_3)_3$, $CH_2COO(CH_2)_3$—$C_2H_5$, $CH_2COO(CH_2)_4$—$C_2H_5$, $CH(CH_3)COOCH_3$, $CH(CH_3)COOC_2H_5$, $CH_2CH_2COOCH_3$, $CH_2CH_2COOC_2H_5$, $CH_2CH_2COOCH_2$—$C_2H_5$, $CH_2CH_2COOCH(CH_3)_2$, $CH_2CH_2COOCH_2CH_2$—$C_2H_5$, 2-(1-methylpropoxycarbonyl)ethyl, 2-(2-methylpropoxycarbonyl)ethyl, $CH_2CH_2COOC(CH_3)_3$, $CH_2CH_2COO(CH_2)_3$—$C_2H_5$, $CH_2CH_2COO(CH_2)_4$—$C_2H_5$, 2-($COOCH_3$)propyl, 2-($COOC_2H_5$)propyl, 2-($COOCH_2$—$C_2H_5$)propyl, 2-[$COOCH(CH_3)_2$]propyl, 2-($COOCH_2CH_2$—$C_2H_5$)propyl, 2-(1-methylpropoxycarbonyl)propyl, 2-(2-methylpropoxycarbonyl)propyl, 2-[$COOC(CH_3)_3$]propyl, 3-($COOCH_3$)propyl, 3-($COOC_2H_5$)propyl, 3-($COOCH_2$—$C_2H_5$)propyl, 3-[$COOCH(CH_3)_2$]propyl, 3-($COOCH_2CH_2$—$C_2H_5$)propyl, 3-(1-methylpropoxycarbonyl)propyl, 3-(2-methylpropoxycarbonyl)propyl, 3-[$COOC(CH_3)_3$]propyl, 3-[$COO(CH_2)_3$—$C_2H_5$]propyl, 3-[$COO(CH_2)_4$—$C_2H_5$]propyl, 2-($COOCH_3$)butyl, 2-($COOC_2H_5$)butyl, 2-($COOCH_2$—$C_2H_5$)butyl, 2-[$COOCH(CH_3)_2$]butyl, 2-($COOCH_2CH_2$—$C_2H_5$)butyl, 2-(1-methylpropoxycarbonyl)butyl, 2-(2-methylpropoxycarbonyl)butyl, 2-[$COOC(CH_3)_3$]butyl, 3-($COOCH_3$)butyl, 3-($COOC_2H_5$)butyl, 3-($COOCH_2$—$C_2H_5$)butyl, 3-[$COOCH(CH_3)_2$]butyl, 3-($COOCH_2CH_2$—$C_2H_5$)butyl, 3-(1-methylpropoxycarbonyl)butyl, 3-(2-methylpropoxycarbonyl)butyl, 3-[$COOC(CH_3)_3$]butyl, 4-($COOCH_3$)butyl, 4-($COOC_2H_5$)butyl, 4-($COOCH_2$—$C_2H_5$)butyl, 4-[$COOCH(CH_3)_2$]butyl, 4-($COOCH_2CH_2$—$C_2H_5$)butyl, 4-(1-methylpropoxycarbonyl)butyl, 4-(2-methylpropoxycarbonyl)butyl, 4-[$COOC(CH_3)_3$]butyl, 4-[$COO(CH_2)_3$–$C_2H_5$]butyl, 4-[$COO(CH_2)_4$—$C_2H_5$]butyl, 5-($COOCH_3$)pentyl, 5-($COOC_2H_5$)pentyl, 5-($COOCH_2$—$C_2H_5$)pentyl, 5-[$COOCH(CH_3)_2$]pentyl, 5-($COOCH_2CH_2$—$C_2H_5$)pentyl, 5-(1-methylpropoxycarbonyl)pentyl, 5-(2-methylpropoxycarbonyl)pentyl, 5-[$COOC(CH_3)_3$]pentyl, 5-[$COO(CH_2)_3$—$C_2H_5$]pentyl, 5-[$COO(CH_2)_4$—$C_2H_5$]pentyl, 6-($COOCH_3$)hexyl, 6-($COOC_2H_5$)hexyl, 6-($COOCH_2$—$C_2H_5$)hexyl, 6-[$COOCH(CH_3)_2$]hexyl, 6-($COOCH_2CH_2$—$C_2H_5$)hexyl, 6-(1-methylpropoxycarbonyl)hexyl, 6-(2-methylpropoxycarbonyl)hexyl, 6-[$COOC(CH_3)_3$]

hexyl, 6-[COO(CH$_2$)$_3$—C$_2$H$_5$]hexyl or 6-[COO(CH$_2$)$_4$—C$_2$H$_5$]hexyl, in particular CH$_2$COOCH$_3$, CH$_2$COOCH(CH$_3$)$_2$ or CH(CH$_3$)COOCH$_3$;

(C$_1$–C$_6$-alkoxy)carbonyl-C$_1$–C$_6$-alkoxy: C$_1$–C$_6$-alkoxy which is substituted by (C$_1$–C$_6$-alkoxy)carbonyl as mentioned above, i.e., for example, OCH$_2$COOCH$_3$, OCH$_2$COOC$_2$H$_5$, OCH$_2$COOCH$_2$—C$_2$H$_5$, OCH$_2$COOCH(CH$_3$)$_2$, OCH$_2$COOCH$_2$CH$_2$—C$_2$H$_5$, (1-methylpropoxycarbonyl)-methoxy, (2-methylpropoxycarbonyl)methoxy, OCH$_2$COOC (CH$_3$)$_3$, OCH$_2$COO(CH$_2$)$_3$—C$_2$H$_5$, OCH$_2$COO(CH$_2$)$_4$—C$_2$H$_5$, OCH(CH$_3$)COOCH$_3$, OCH(CH$_3$)COOC$_2$H$_5$, OCH$_2$CH$_2$COOCH$_3$, OCH$_2$CH$_2$COOC$_2$H$_5$, OCH$_2$CH$_2$COOCH$_2$—C$_2$H$_5$, OCH$_2$CH$_2$COOCH(CH$_3$)$_2$, OCH$_2$CH$_2$COOCH$_2$CH$_2$—C$_2$H$_5$, 2-(1-methylpropoxycarbonyl)ethoxy, 2-(2-methylpropoxycarbonyl)ethoxy, OCH$_2$CH$_2$COOC(CH$_3$)$_3$, OCH$_2$CH$_2$COO(CH$_2$)$_3$—C$_2$H$_5$, OCH$_2$CH$_2$COO(CH$_2$)$_4$—C$_2$H$_5$, 2-(COOCH$_3$)propoxy, 2-(COOC$_2$H$_5$)propoxy, 2-(COOCH$_2$—C$_2$H$_5$)propoxy, 2-[COOCH(CH$_3$)$_2$]propoxy, 2-(COOCH$_2$CH$_2$—C$_2$H$_5$) propoxy, 2-(1-methylpropoxycarbonyl)propoxy, 2-(2-methylpropoxycarbonyl)propoxy, 2-[COOC(CH$_3$)$_3$] propoxy, 3-(COOCH$_3$)propoxy, 3-(COOC$_2$H$_5$) propoxy, 3-(COOCH$_2$—C$_2$H$_5$)propoxy, 3-[COOCH(CH$_3$)$_2$]propoxy, 3-(COOCH$_2$CH$_2$—C$_2$H$_5$)propoxy, 3-(1-methylpropoxycarbonyl)propoxy, 3-(2-methylpropoxycarbonyl)propoxy, 3-[COOC(CH$_3$)$_3$] propoxy, 3-[COO(CH$_2$)$_3$—C$_2$H$_5$]propoxy, 3-[COO(CH$_2$)$_4$—C$_2$H$_5$]propoxy, 2-(COOCH$_3$)butoxy, 2-(COOC$_2$H$_5$)butoxy, 2-(COOCH$_2$—C$_2$H$_5$)butoxy, 2-[COOCH(CH$_3$)$_2$]butoxy, 2-(COOCH$_2$CH$_2$—C$_2$H$_5$) butoxy, 2-(1-methylpropoxycarbonyl)butoxy, 2-(2-methylpropoxycarbonyl)butoxy, 2-[COOC(CH$_3$)$_3$] butoxy, 3-(COOCH$_3$)butoxy, 3-(COOC$_2$H$_5$)butoxy, 3-(COOCH$_2$—C$_2$H$_5$)butoxy, 3-[COOCH(CH$_3$)$_2$] butoxy, 3-(COOCH$_2$CH$_2$—C$_2$H$_5$)butoxy, 3-(1-methylpropoxycarbonyl)butoxy, 3-(2-methylpropoxycarbonyl)butoxy, 3-[COOC(CH$_3$)$_3$] butoxy, 4-(COOCH$_3$)butoxy, 4-(COOC$_2$H$_5$)butoxy, 4-(COOCH$_2$—C$_2$H$_5$)butoxy, 4-[COOCH(CH$_3$)$_2$] butoxy, 4-(COOCH$_2$CH$_2$—C$_2$H$_5$)butoxy, 4-(1-methylpropoxycarbonyl)butoxy, 4-(2-methylpropoxycarbonyl)butoxy, 4-[COOC(CH$_3$)$_3$] butoxy, 4-[COO(CH$_2$)$_3$—C$_2$H$_5$]butoxy, 4-[COO(CH$_2$)$_4$—C$_2$H$_5$]butoxy, 5-(COOCH$_3$)pentoxy, 5-(COOC$_2$H$_5$) pentoxy, 5-(COOCH$_2$—C$_2$H$_5$)pentoxy, 5-[COOCH(CH$_3$)$_2$]pentoxy, 5-(COOCH$_2$CH$_2$—C$_2$H$_5$)pentoxy, 5-(1-methylpropoxycarbonyl)pentoxy, 5-(2-methylpropoxycarbonyl)pentoxy, 5-[COOC(CH$_3$)$_3$] pentoxy, 5-[COO(CH)$_3$—C$_2$H$_5$]pentoxy, 5-[COO(CH$_2$)$_4$—C$_2$H$_5$]pentoxy, 6-(COOCH$_3$)hexoxy, 6-(COOC$_2$H$_5$)hexoxy, 6-(COOCH$_2$—C$_2$H$_5$)hexoxy, 6-[COOCH(CH$_3$)$_2$]hexoxy, 6-(COOCH$_2$CH$_2$—C$_2$H$_5$) hexoxy, 6-(1methylpropoxycarbonyl)hexoxy, 6-(2-methylpropoxycarbonyl)hexoxy, 6-[COOC(CH$_3$)$_3$] hexoxy, 6-(COO(CH$_2$)$_3$—C$_2$H$_5$]hexoxy or 6-[COO(CH$_2$)$_4$—C$_2$H$_5$]hexoxy, in particular OCH$_2$COOCH$_3$, OCH$_2$COOCH(CH$_3$)$_2$, OCH(CH$_3$)COOCH$_3$ or OCH$_2$CH$_2$COOCH$_3$;

C$_1$–C$_6$-alkylsulfinyl: for example SOCH$_3$, SOC$_2$H$_5$, SOCH$_2$—C$_2$H$_5$, SOCH(CH$_3$)$_2$, n-butylsulfinyl, SOCH(CH$_3$)—C$_2$H$_5$—SOCH$_2$—CH(CH$_3$)$_2$, SOC(CH$_3$)$_3$, n-pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, n-Hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular SOCH$_3$ or SOC$_2$H$_5$;

C$_1$–C$_6$-alkylsulfonyl: for example SO$_2$CH$_3$, SO$_2$C$_2$H$_5$, SO$_2$CH$_2$—C$_2$H$_5$, SO$_2$CH(CH$_3$)$_2$, n-butylsulfonyl, SO$_2$CH(CH$_3$)—C$_2$H$_5$, SO$_2$CH$_2$—CH(CH$_3$)$_2$, SO$_2$C(CH$_3$)$_3$, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, n-hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in part icular SO$_2$CH$_3$ or SO$_2$C$_2$H$_5$;

C$_1$–C$_6$-haloalkylsulfonyl: C$_1$–C$_6$-alkylsulfonyl as mentioned above which is partially or fully substituted by fluorine, chlorine, bromine and/or iodine, i.e., for example, ClCH$_2$—SO$_2$—, CH(Cl)$_2$—SO$_2$—, C(Cl)$_3$—SO$_2$—, FCH$_2$—SO$_2$—, CHF$_2$—SO$_2$—, CF$_3$—SO$_2$—, chlorofluoromethyl-SO$_2$—, dichlorofluoromethyl-SO$_2$—, chlorodifluoromethyl-SO$_2$—, 1-fluoroethyl-SO$_2$—, 2-fluoroethyl-SO$_2$—, 2-chloroethyl-SO$_2$—, 2-bromoethyl-SO$_2$—, 2-iodoethyl-SO$_2$—, 2,2-difluoroethyl-SO$_2$—, 2,2,2-trifluoroethyl-SO$_2$—, 2-chloro-2-fluoroethyl-SO$_2$—, 2-chloro-2,2-difluoroethyl-SO$_2$—, 2,2-dichloro-2-fluoroethyl-SO$_2$—, 2,2,2-trichloroethyl-SO$_2$—, C$_2$F$_5$—SO$_2$—, 2-fluoropropyl-SO$_2$—, 3-fluoropropyl-SO$_2$—, 2,2-difluoropropyl-SO$_2$—, 2,3-difluoropropyl-SO$_2$—, 2-chloropropyl-SO$_2$—, 3-chloropropyl-SO$_2$—, 2,3-dichloropropyl-SO$_2$—, 2-bromopropyl-SO$_2$—, 3-bromopropyl-SO$_2$—, 3,3,3-trifluoropropyl-SO$_2$—, 3,3,3-trichloropropyl-SO$_2$—, 2,2,3,3,3-pentafluoropropyl-SO$_2$—, C$_2$F$_5$—CF$_2$—SO$_2$—, 1-(fluoromethyl)-2-fluoroethyl-SO$_2$—, 1-(chloromethyl)-2-chloroethyl-SO$_2$—, 1-(bromomethyl)-2-bromoethyl-SO$_2$—, 4-fluorobutyl-SO$_2$—, 4-chlorobutyl-SO$_2$—, 4-bromobutyl-SO$_2$—, C$_2$F$_5$—CF$_2$—CF$_2$—SO$_2$—, 5-fluoropentyl-SO$_2$—, 5-chloropentyl-SO$_2$—, 5-bromopentyl-SO$_2$—, 5-iodopentyl-SO$_2$—, 5,5,5-trichloropentyl-SO$_2$—, C$_2$F$_5$—CF$_2$—CF$_2$-CF$_2$—SO$_2$—, 6-fluorohexyl-SO$_2$—, 6-chlorohexyl-SO$_2$—, 6-bromohexyl-SO$_2$—, 6-iodohexyl-SO$_2$—, 6,6,6-trichlorohexyl-SO$_2$— or dodecafluorohexyl-SO$_2$—, in particular CF$_3$—SO$_2$—;

C$_3$–C$_6$-alkenyl: for example prop-1-en-1-yl, allyl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, in particular allyl;

$C_3-C_6$-alkynyl: for example prop-1-yn-1-yl, propargyl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-in-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular propargyl;

$C_3-C_6$-alkenyloxy: for example prop-1-en-1-yloxy, allyloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-2-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular allyloxy;

$C_3-C_6$-alkynyloxy: for example prop-1-yn-1-yloxy, propargyloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methyl-but-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular propargyloxy.

With a view to the use of the substituted 2-phenylpyridine I as herbicides and/or as compounds having desiccant/defoliant action, the variables preferably have the following meanings, in each case on their own or in combination:

n is zero;

$R^1$ is $C_1-C_6$-alkylsulfonyl, in particular $SO_2CH_3$;

$R^2$ is halogen, in particular chlorine;

$R^3$ is hydrogen, fluorine or chlorine, particularly preferably fluorine or chlorine, in particular fluorine;

$R^4$ is cyano or halogen, particularly preferably cyano or chlorine, in particular chlorine;

$R^5$ is hydrogen, nitro, cyano, hydroxylamino, $C_1-C_6$-alkyl (in particular $CH_3$), $C_1-C_6$-haloalkyl (in particular halomethyl), —COCl, —CO—$OR^6$, —CCO—O—($C_1-C_4$-alkylene)—CO—$OR^6$, —O—($C_1-C_4$-alkylene)—CO—$OR^6$, —O—($C_1-C_4$-alkylene)—CO—O—($C_1-C_4$-alkylene)—CO—$OR^6$, —$COR^9$, formyl, —CH=N—$OR^{15}$ or —$CNH_2$, particularly preferably —CO—$OR^6$, —CO—O—($C_1-C_4$-alkylene)—CO—$OR^6$, —CO—($C_1-C_4$-alkylene)—CO—$OR^6$ or —$OR^9$;

$R^6$ is hydrogen, $C_1-C_6$-alkyl, $C_3-C_6$-alkenyl, $C_3-C_6$-alkynyl or $C_1-C_6$-alkoxy-$C_1-C_6$-alkyl;

$R^9$ is hydrogen, $C_1-C_6$-alkyl, $C_3-C_6$-alkenyl or $C_3-C_6$-alkynyl;

$R^{15}$ is $C_1-C_6$-alkyl.

Very particular preference is given to the compounds of the formula Ia (=I where n=zero; $R^1$=methylsulfonyl; $R^2$ and $R^4$=chlorine; $R^3$=fluorine), in particular to the compounds of Table 1:

TABLE 1

Ia

[Structure: pyridine ring with H₃C—SO₂—O— substituent, Cl, and attached to phenyl ring bearing F, Cl, and R⁵]

| No. | R⁵ |
|---|---|
| Ia.1 | —H |
| Ia.2 | —F |
| Ia.3 | —Cl |
| Ia.4 | —Br |
| Ia.5 | —I |
| Ia.6 | —CN |
| Ia.7 | —CH₃ |
| Ia.8 | —CH₂Cl |
| Ia.9 | —CHCl₂ |
| Ia.10 | —CCl₃ |
| Ia.11 | —CH₂Br |
| Ia.12 | —CHBr₂ |
| Ia.13 | —COCl |
| Ia.14 | —CO—OH |
| Ia.15 | —CO—OCH₃ |
| Ia.16 | —CO—OC₂H₅ |
| Ia.17 | —CO—OCH₂—C₂H₅ |
| Ia.18 | —CO—OCH(CH₃)₂ |
| Ia.19 | —CO—OCH₂—CH₂—C₂H₅ |
| Ia.20 | —CO—OCH₂—CH(CH₃)₂ |
| Ia.21 | —CO—OCH₂—CH₂—CH₂—C₂H₅ |
| Ia.22 | —CO—OCH₂—CCl₃ |
| Ia.23 | —CO—OCH₂—CF₃ |
| Ia.24 | —CO—OCH₂—CH=CH₂ |
| Ia.25 | —CO—OCH₂—CH=CH—CH₃ |
| Ia.26 | —CO—OCH₂—CH₂—CH=CH₂ |
| Ia.27 | —CO—OCH(CH₃)—CH=CH₂ |
| Ia.28 | —CO—OCH₂—CH₂—CH₂—CH=CH₂ |
| Ia.29 | —CO—OCH₂—CH=C(CH₃)₂ |
| Ia.30 | —CO—OCH₂—C(CH₃)=CH—CH₃ |
| Ia.31 | —CO—OCH₂—C≡CH |
| Ia.32 | —CO—OCH(CH₃)—C≡CH |
| Ia.33 | —CO—OCH₂—C≡C—CH₃ |
| Ia.34 | —CO—OCH₂—C≡C—C₂H₅ |
| Ia.35 | —CO—O-cyclopropyl |
| Ia.36 | —CO—O-cyclobutyl |
| Ia.37 | —CO—O-cyclopentyl |
| Ia.38 | —CO—O-cyclohexyl |
| Ia.39 | —CO—OCH₂—CH₂—OCH₃ |
| Ia.40 | —CO—OCH₂—CH₂—OC₂H₅ |
| Ia.41 | —CO—OCH₂—CH₂—OCH₂—CH₂—CH₃ |
| Ia.42 | —CO—OCH₂—CH₂—OCH(CH₃)₂ |
| Ia.43 | —CO—NH₂ |
| Ia.44 | —CO—NH—CH₃ |
| Ia.45 | —CO—N(CH₃)₂ |
| Ia.46 | —CO—NH—CH₂—CO—OH |
| Ia.47 | —CO—NH—CH₂—CO—OCH₃ |
| Ia.48 | —CO—NH—CH₂—CO—OC₂H₅ |
| Ia.49 | —CO—NH—CH₂—CO—OCH₂—C₂H₅ |
| Ia.50 | —CO—NH—CH₂—CO—OCH₂—CH₂—C₂H₅ |
| Ia.51 | —CO—NH—CH(CH₃)—CO—OH |
| Ia.52 | —CO—NH—CH(CH₃)—CO—OCH₃ |
| Ia.53 | —CO—NH—CH(CH₃)—CO—OC₂H₅ |
| Ia.54 | —CO—NH—CH(CH₃)—CO—OCH₂—C₂H₅ |
| Ia.55 | —CO—NH—CH(CH₃)—CO—OCH₂—CH₂—C₂H₅ |
| Ia.56 | —CO—N(CH₃)—CH₂—CO—OH |
| Ia.57 | —CO—N(CH₃)—CH₂—CO—OCH₃ |
| Ia.58 | —CO—N(CH₃)—CH₂—CO—OC₂H₅ |
| Ia.59 | —CO—N(CH₃)—CH₂—CO—OCH₂—C₂H₅ |
| Ia.60 | —CO—N(CH₃)—CH₂—CO—OCH₂—CH₂—C₂H₅ |
| Ia.61 | —CO—N(CH₃)—CH(CH₃)—CO—OH |
| Ia.62 | —CO—N(CH₃)—CH(CH₃)—CO—OCH₃ |
| Ia.63 | —CO—N(CH₃)—CH(CH₃)—CO—OC₂H₅ |
| Ia.64 | —CO—N(CH₃)—CH(CH₃)—CO—OCH₂—C₂H₅ |

TABLE 1-continued

Ia

[Structure: pyridine ring with H3C—SO2—O— at one position, Cl at another, connected to a phenyl ring bearing F, Cl, and R5 substituents]

| No. | R⁵ |
|---|---|
| Ia.65 | —CO—N(CH₃)—CH(CH₃)—CO—OCH₂—CH₂—C₂H₅ |
| Ia.66 | —CO—OCH₂—CO—OH |
| Ia.67 | —CO—OCH₂—CO—OCH₃ |
| Ia.68 | —CO—OCH₂—CO—OC₂H₅ |
| Ia.69 | —CO—OCH₂—CO—OCH₂—C₂H₅ |
| Ia.70 | —CO—OCH₂—CO—OCH(CH₃)₂ |
| Ia.71 | —CO—OCH₂—CO—OCH₂—CH₂—C₂H₅ |
| Ia.72 | —CO—OCH₂—CO—OCH₂—CH₂—CH(CH₃)₂ |
| Ia.73 | —CO—OCH₂—CO—OCH(CH₃)—C₂H₅ |
| Ia.74 | —CO—OCH₂—CO—OC(CH₃)₃ |
| Ia.75 | —CO—OCH₂—CO—OCH₂—CH₂—CH₂—C₂H₅ |
| Ia.76 | —CO—OCH₂—CO—OCH₂—CH₂—CH(CH₃)₂ |
| Ia.77 | —CO—OCH(CH₃)—CO—OH |
| Ia.78 | —CO—OCH(CH₃)—CO—OCH₃ |
| Ia.79 | —CO—OCH(CH₃)—CO—OC₂H₅ |
| Ia.80 | —CO—OCH(CH₃)—CO—OCH₂—C₂H₅ |
| Ia.81 | —CO—OCH(CH₃)—CO—OCH(CH₃)₂ |
| Ia.82 | —CO—OCH(CH₃)—CO—OCH₂—CH₂—C₂H₅ |
| Ia.83 | —CO—OCH(CH₃)—CO—OCH₂—CH(CH₃)₂ |
| Ia.84 | —CO—OCH(CH₃)—CO—OCH(CH₃)—C₂H₅ |
| Ia.85 | —CO—OCH(CH₃)—CO—OC(CH₃)₃ |
| Ia.86 | —CO—OCH(CH₃)—CO—OCH₂—CH₂—CH₂—C₂H₅ |
| Ia.87 | —CO—OCH(CH₃)—CO—OCH₂—CH₂—CH(CH₃)₂ |
| Ia.88 | —CO—OCH₂—CO—NH₂ |
| Ia.89 | —CO—OCH₂—CO—NH—CH₃ |
| Ia.90 | —CO—OCH₂—CO—N(CH₃)₂ |
| Ia.91 | —CO—OCH₂—CO—N(CH₃)—CH₂—CO—OH |
| Ia.92 | —CO—OCH₂—CO—N(CH₃)—CH₂—CO—OCH₃ |
| Ia.93 | —CO—OCH₂—CO—N(CH₃)—CH₂—CO—OC₂H₅ |
| Ia.94 | —CO—OCH(CH₃)—CO—NH₂ |
| Ia.95 | —CO—OCH(CH₃)—CO—NH—CH₃ |
| Ia.96 | —CO—OCH(CH₃)—CO—N(CH₃)₂ |
| Ia.97 | —CO—OCH(CH₃)—CO—N(CH₃)—CH₂—CO—OH |
| Ia.98 | —CO—OCH(CH₃)—CO—N(CH₃)—CH₂—CO—OCH₃ |
| Ia.99 | —CO—OCH(CH₃)—CO—N(CH₃)—CH₂—CO—OC₂H₅ |
| Ia.100 | —OCH₂—CHO |
| Ia.101 | —OCH₂—CO—CH₃ |
| Ia.102 | —OCH₂—CO—C₂H₅ |
| Ia.103 | —OCH₂—CO—CH(CH₃)₂ |
| Ia.104 | —OCH₂—CO—CH₂—C₂H₅ |
| Ia.105 | —OCH₂—CO—CH₂—CH₂—C₂H₅ |
| Ia.106 | —OCH₂—CO—CH₂—CH(CH₃)₂ |
| Ia.107 | —OCH₂—CO—CH(CH₃)—C₂H₅ |
| Ia.108 | —OCH₂—CO—C(CH₃)₃ |
| Ia.109 | —OCH(CH₃)—CO—CH₃ |
| Ia.110 | —OCH(CH₃)—CO—C₂H₅ |
| Ia.111 | —OCH(CH₃)—CO—CH₂—C₂H₅ |
| Ia.112 | —OCH(CH₃)—CO—CH(CH₃)₂ |
| Ia.113 | —OCH(CH₃)—CO—CH₂—CH₂—C₂H₅ |
| Ia.114 | —OCH(CH₃)—CO—CH₂—CH(CH₃)₂ |
| Ia.115 | —OCH(CH₃)—CO—CH(CH₃)—C₂H₅ |
| Ia.116 | —OCH(CH₃)—CO—C(CH₃)₃ |
| Ia.117 | —OCH₂—CO—CH₂—Cl |
| Ia.118 | —OCH(CH₃)—CO—CH₂—Cl |
| Ia.119 | —OCH₂—CO—CH₂—CH=CH₂ |
| Ia.120 | —OCH(CH₃)—CO—CH₂—CH=CH₂ |
| Ia.121 | —OCH₂—CO—CH₂—C≡CH |
| Ia.122 | —OCH(CH₃)—CO—CH₂—C≡CH |
| Ia.123 | —OCH₂—CO-cyclopentyl |
| Ia.124 | —OCH(CH₃)—CO-cyclohexyl |
| Ia.125 | —OCH₂—CO—CH₂—OCH₃ |
| Ia.126 | —OCH(CH₃)—CO—CH₂—OCH₃ |
| Ia.127 | —OCH₂—CO—CH₂—OC₂H₅ |
| Ia.128 | —OCH(CH₃)—CO—CH₂—OC₂H₅ |

TABLE 1-continued

Ia

[Structure: pyridine ring with H₃C—SO₂—O— at 5-position, Cl at 3-position, and at 2-position a phenyl group bearing F (ortho), Cl (para), and R⁵ (meta to Cl)]

| No. | R⁵ |
|---|---|
| Ia.129 | —OCH₂—CO—CH₂—CH₂—OCH₃ |
| Ia.130 | —OCH(CH₃)—CO—CH₂—CH₂—OCH₃ |
| Ia.131 | —OCH₂—CO—CH₂—CH₂—OC₂H₅ |
| Ia.132 | —OCH(CH₃)—CO—CH₂—CH₂—OC₂H₅ |
| Ia.133 | —SCH₂—CHO |
| Ia.134 | —SCH₂—CO—CH₃ |
| Ia.135 | —SCH₂—CO—C₂H₅ |
| Ia.136 | —SCH₂—CO—CH(CH₃)₂ |
| Ia.137 | —SCH₂—CO—CH₂—C₂H₅ |
| Ia.138 | —SCH(CH₃)—CO—CH₂—CH₂—C₂H₅ |
| Ia.139 | —SCH(CH₃)—CO—CH₂—CH(CH₃)₂ |
| Ia.140 | —SCH(CH₃)—CO—CH(CH₃)—C₂H₅ |
| Ia.141 | —SCH(CH₃)—CO—C(CH₃)₃ |
| Ia.142 | —SCH₂—CO—CH₂—CH=CH₂ |
| Ia.143 | —SCH(CH₃)—CO—CH₂—CH=CH₂ |
| Ia.144 | —SCH₂—CO—CH₂—CH≡CH |
| Ia.145 | —SCH(CH₃)—CO—CH₂—CH≡CH |
| Ia.146 | —SCH₂—CO-cyclopentyl |
| Ia.147 | —SCH(CH₃)—CO-cyclopentyl |
| Ia.148 | —SCH₂—CO-cyclohexyl |
| Ia.149 | —SCH(CH₃)—CO-cyclohexyl |
| Ia.150 | —SCH₂—CO—CH₂—OCH₃ |
| Ia.151 | —SCH(CH₃)—CO—CH₂—OCH₃ |
| Ia.152 | —SCH₂—CO—CH₂—OC₂H₅ |
| Ia.153 | —SCH(CH₃)—CO—CH₂—OC₂H₅ |
| Ia.154 | —SCH₂—CO—CH₂—CH₂—OCH₃ |
| Ia.155 | —SCH(CH₃)—CO—CH₂—CH₂—OCH₃ |
| Ia.156 | —SCH₂—CO—CH₂—CH₂—OC₂H₅ |
| Ia.157 | —SCH(CH₃)—CO—CH₂—CH₂—OC₂H₅ |
| Ia.158 | —OCH₂—CO—OH |
| Ia.159 | —OCH₂—CO—OCH₃ |
| Ia.160 | —OCH₂—CO—OC₂H₅ |
| Ia.161 | —OCH₂—CO—OCH₂—C₂H₅ |
| Ia.162 | —OCH₂—CO—OCH(CH₃)₂ |
| Ia.163 | —OCH₂—CO—OCH₂—CH₂—C₂H₅ |
| Ia.164 | —OCH₂—CO—OCH₂—CH(CH₃)₂ |
| Ia.165 | —OCH₂—CO—OC(CH₃)₃ |
| Ia.166 | —OCH₂—CO—OCH₂—CH₂—CH₂—C₂H₅ |
| Ia.167 | —OCH₂—CO—OCH₂—CH₂—CH(CH₃)₂ |
| Ia.168 | —OCH(CH₃)—CO—OH |
| Ia.169 | —OCH(CH₃)—CO—OCH₃ |
| Ia.170 | —OCH(CH₃)—CO—OC₂H₅ |
| Ia.171 | —OCH(CH₃)—CO—OCH₂—OC₂H₅ |
| Ia.172 | —OCH(CH₃)—CO—OCH(CH₃)₂ |
| Ia.173 | —OCH(CH₃)—CO—OCH₂—CH₂—C₂H₅ |
| Ia.174 | —OCH(CH₃)—CO—OCH₂—CH(CH₃)₂ |
| Ia.175 | —OCH(CH₃)—CO—OC(CH₃)₃ |
| Ia.176 | —OCH(CH₃)—CO—OCH₂—CH₂—CH₂—C₂H₅ |
| Ia.177 | —OCH(CH₃)—CO—OCH₂—CH₂—CH(CH₃)₂ |
| Ia.178 | —SCH₂—CO—OH |
| Ia.179 | —SCH₂—CO—OCH₃ |
| Ia.180 | —SCH₂—CO—OC₂H₅ |
| Ia.181 | —SCH₂—CO—OCH₂—C₂H₅ |
| Ia.182 | —SCH₂—CO—OCH(CH₃)₂ |
| Ia.183 | —SCH₂—CO—OCH₂—CH₂—C₂H₅ |
| Ia.184 | —SCH₂—CO—OCH₂—CH(CH₃)₂ |
| Ia.185 | —SCH₂—CO—OC(CH₃)₃ |
| Ia.186 | —SCH₂—CO—OCH₂—CH₂—CH₂—C₂H₅ |
| Ia.187 | —SCH₂—CO—OCH₂—CH₂—CH(CH₃)₂ |
| Ia.188 | —SCH(CH₃)—CO—OH |
| Ia.189 | —SCH(CH₃)—CO—OCH₃ |
| Ia.190 | —SCH(CH₃)—CO—OC₂H₅ |
| Ia.191 | —SCH(CH₃)—CO—OCH₂—C₂H₅ |
| Ia.192 | —SCH(CH₃)—CO—OCH(CH₃)₂ |

TABLE 1-continued

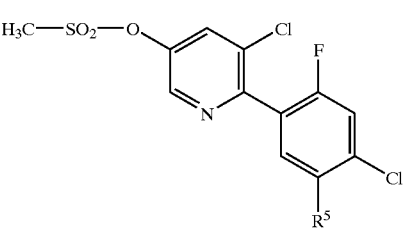

Ia

| No. | R⁵ |
|---|---|
| Ia.193 | —SCH(CH₃)—CO—OCH₂—CH₂—C₂H₅ |
| Ia.194 | —SCH(CH₃)—CO—OCH₂—CH(CH₃)₂ |
| Ia.195 | —SCH(CH₃)—CO—OC(CH₃)₃ |
| Ia.196 | —SCH(CH₃)—CO—OCH₂—CH₂—CH₂—C₂H₅ |
| Ia.197 | —SCH(CH₃)—CO—OCH₂—CH₂—CH(CH₃)₂ |
| Ia.198 | —OCH₂—CO—OCH₂—CO—OH |
| Ia.199 | —OCH₂—CO—OCH₂—CO—OCH₃ |
| Ia.200 | —OCH₂—CO—OCH₂—CO—OC₂H₅ |
| Ia.201 | —OCH₂—CO—OCH₂—CO—OCH₂—C₂H₅ |
| Ia.202 | —OCH₂—CO—OCH₂—CO—OCH(CH₃)₂ |
| Ia.203 | —OCH₂—CO—OCH₂—CO—OCH₂—CH₂—C₂H₅ |
| Ia.204 | —OCH₂—CO—OCH₂—CO—OCH₂—CH(CH₃)₂ |
| Ia.205 | —OCH₂—CO—OCH₂—CO—OCH(CH₃)—C₂H₅ |
| Ia.206 | —OCH₂—CO—OCH₂—CO—OC(CH₃)₃ |
| Ia.207 | I>—OCH₂—CO—OCH(CH₃)—CO—OH |
| Ia.208 | —OCH₂—CO₂—CH(CH₃)—CO—OCH₃ |
| Ia.209 | —OCH₂—CO—OCH(CH₃)—CO—OC₂H₅ |
| Ia.210 | —OCH₂—CO—OCH(CH₃)—CO—OCH₂—C₂H₅ |
| Ia.211 | —OCH₂—CO—OCH(CH₃)—CO—OCH(CH₃)₂ |
| Ia.212 | —OCH₂—CO—OCH(CH₃)—CO—OCH₂—CH₂—C₂H₅ |
| Ia.213 | —OCH₂—CO—OCH(CH₃)—CO—OCH₂—CH(CH₃)₂ |
| Ia.214 | —OCH₂—CO—OCH(CH₃)—CO—OCH(CH₃)—C₂H₅ |
| Ia.215 | —OCH₂—CO—OCH(CH₃)—CO—OC(CH₃)₃ |
| Ia.216 | —OCH(CH₃)—CO—OCH₂—CO—OH |
| Ia.217 | —OCH(CH₃)—CO—OCH₂—CO—OCH₃ |
| Ia.218 | —OCH(CH₃)—CO—OCH₂—CO—OC₂H₅ |
| Ia.219 | —OCH(CH₃)—CO—OCH₂—CO—OCH₂—C₂H₅ |
| Ia.220 | —OCH(CH₃)—CO—OCH₂—CO—OCH(CH₃)₂ |
| Ia.221 | —OCH(CH₃)—CO—OCH₂—CO—OCH₂—CH₂—C₂H₅ |
| Ia.222 | —OCH(CH₃)—CO—OCH₂—CO—OCH₂—CH(CH₃)₂ |
| Ia.223 | —OCH(CH₃)—CO—OCH₂—CO—OCH(CH₃)—C₂H₅ |
| Ia.224 | —OCH(CH₃)—CO—OCH₂—CO—OC(CH₃)₃ |
| Ia.225 | —OCH(CH₃)—CO—OCH(CH₃)—CO—OH |
| Ia.226 | —OCH(CH₃)—CO—OCH(CH₃)—CO—OCH₃ |
| Ia.227 | —OCH(CH₃)—CO—OCH(CH₃)—CO—OC₂H₅ |
| Ia.228 | —OCH(CH₃)—CO—OCH(CH₃)—CO—OCH₂—C₂H₅ |
| Ia.229 | —OCH(CH₃)—CO—OCH(CH₃)—CO—OCH(CH₃)₂ |
| Ia.230 | —OCH(CH₃)—CO—OCH(CH₃)—CO—OCH₂—CH₂—C₂H₅ |
| Ia.231 | —OCH(CH₃)—CO—OCH(CH₃)—CO—OCH₂—CH(CH₃)₂ |
| Ia.232 | —OCH(CH₃)—CO—OCH(CH₃)—CO—OCH(CH₃)—C₂H₅ |
| Ia.233 | —OCH(CH₃)—CO—OCH(CH₃)—CO—OC(CH₃)₃ |
| Ia.234 | —SCH₂—CO—OCH₂—CO—OH |
| Ia.235 | —SCH₂—CO—OCH₂—CO—OCH₃ |
| Ia.236 | —SCH₂—CO—OCH₂—CO—OC₂H₅ |
| Ia.237 | —SCH₂—CO—OCH₂—CO—OCH₂—C₂H₅ |
| Ia.238 | —SCH₂—CO—OCH₂—CO—OCH(CH₃)₂ |
| Ia.239 | —SCH₂—CO—OCH₂—CO—OCH₂—CH₂—C₂H₅ |
| Ia.240 | —SCH₂—CO—OCH₂—CO—OCH₂—CH(CH₃)₂ |
| Ia.241 | —SCH₂—CO—OCH₂—CO—OCH(CH₃)—C₂H₅ |
| Ia.242 | —SCH₂—CO—OCH₂—CO—OC(CH₃)₃ |
| Ia.243 | —SCH₂—CO—OCH(CH₃)—CO—OH |
| Ia.244 | —SCH₂—CO—OCH(CH₃)—CO—OCH₃ |
| Ia.245 | —SCH₂—CO—OCH(CH₃)—CO—OC₂H₅ |
| Ia.246 | —SCH₂—CO—OCH(CH₃)—CO—OCH₂—C₂H₅ |
| Ia.247 | —SCH₂—CO—OCH(CH₃)—CO—OCH(CH₃)₂ |
| Ia.248 | —SCH₂—CO—OCH(CH₃)—CO—OCH₂—CH₂—C₂H₅ |
| Ia.249 | —SCH₂—CO—OCH(CH₃)—CO—OCH₂—CH(CH₃)₂ |
| Ia.250 | —SCH₂—CO—OCH(CH₃)—CO—OCH(CH₃)—C₂H₅ |
| Ia.251 | —SCH₂—CO—OCH(CH₃)—CO—OC(CH₃)₃ |
| Ia.252 | —SCH(CH₃)—CO—OCH₂—CO—OH |
| Ia.253 | —SCH(CH₃)—CO—OCH₂—CO—OCH₃ |
| Ia.254 | —SCH(CH₃)—CO—OCH₂—CO—OC₂H₅ |
| Ia.255 | —SCH(CH₃)—CO—OCH₂—CO—OCH₂—C₂H₅ |
| Ia.256 | —SCH(CH₃)—CO—OCH₂—CO—OCH(CH₃)₂ |

TABLE 1-continued

Ia (Structure: pyridine with H$_3$C—SO$_2$—O— at 5-position, Cl at 3-position, and 2-(2-fluoro-4-chloro-5-R$^5$-phenyl) substituent)

| No. | R$^5$ |
|---|---|
| Ia.257 | —SCH(CH$_3$)—CO—OCH$_2$—CO—OCH$_2$—CH$_2$—C$_2$H$_5$ |
| Ia.258 | —SCH(CH$_3$)—CO—OCH$_2$—CO—OCH$_2$—CH(CH$_3$)$_2$ |
| Ia.259 | —SCH(CH$_3$)—CO—OCH$_2$—CO—OCH(CH$_3$)—C$_2$H$_5$ |
| Ia.260 | —SCH(CH$_3$)—CO—OCH$_2$—CO—OC(CH$_3$)$_3$ |
| Ia.261 | —SCH(CH$_3$)—CO—OCH(CH$_3$)—CO—OH |
| Ia.262 | —SCH(CH$_3$)—CO—OCH(CH$_3$)—CO—OCH$_3$ |
| Ia.263 | —SCH(CH$_3$)—CO—OCH(CH$_3$)—CO—OC$_2$H$_5$ |
| Ia.264 | —SCH(CH$_3$)—CO—OCH(CH$_3$)—CO—OCH$_2$—C$_2$H$_5$ |
| Ia.265 | —SCH(CH$_3$)—CO—OCH(CH$_3$)—CO—OCH(CH$_3$)$_2$ |
| Ia.266 | —SCH(CH$_3$)—CO—OCH(CH$_3$)—CO—OCH$_2$—CH$_2$—C$_2$H$_5$ |
| Ia.267 | —SCH(CH$_3$)—CO—OCH(CH$_3$)—CO—OCH$_2$—CH(CH$_3$)$_2$ |
| Ia.268 | —SCH(CH$_3$)—CO—OCH(CH$_3$)—CO—OCH(CH$_3$)—C$_2$H$_5$ |
| Ia.269 | —SCH(CH$_3$)—CO—OCH(CH$_3$)—CO—OC(CH$_3$)$_3$ |
| Ia.270 | —OCH$_2$—CO—NH$_2$ |
| Ia.271 | —OCH$_2$—CO—NH—CH$_3$ |
| Ia.272 | —OCH$_2$—CO—N(CH$_3$)$_2$ |
| Ia.273 | —OCH$_2$—CO—NH—CH$_2$—CO—OH |
| Ia.274 | —OCH$_2$—CO—NH—CH$_2$—CO—OCH$_3$ |
| Ia.275 | —OCH$_2$—CO—NH—CH$_2$—CO—OC$_2$H$_5$ |
| Ia.276 | —OCH$_2$—CO—NH—CH$_2$—CO—OCH$_2$—C$_2$H$_5$ |
| Ia.277 | —OCH$_2$—CO—NH—CH$_2$—CO—OCH$_2$—CH$_2$—C$_2$H$_5$ |
| Ia.278 | —OCH$_2$—CO—NH—CH(CH$_3$)—CO—OH |
| Ia.279 | —OCH$_2$—CO—NH—CH(CH$_3$)—CO—OCH$_3$ |
| Ia.280 | —OCH$_2$—CO—NH—CH(CH$_3$)—CO—OC$_2$H$_5$ |
| Ia.281 | —OCH$_2$—CO—NH—CH(CH$_3$)—CO—OCH$_2$—C$_2$H$_5$ |
| Ia.282 | —OCH$_2$—CO—NH—CH(CH$_3$)—CO—OCH$_2$—CH$_2$—C$_2$H$_5$ |
| Ia.283 | —OCH$_2$—CO—N(CH$_3$)—CH$_2$—CO—OH |
| Ia.284 | —OCH$_2$—CO—N(CH$_3$)—CH$_2$—CO—OCH$_3$ |
| Ia.285 | —OCH$_2$—CO—N(CH$_3$)—CH$_2$—CO—OC$_2$H$_5$ |
| Ia.286 | —OCH$_2$—CO—N(CH$_3$)—CH$_2$—CO—OCH$_2$—C$_2$H$_5$ |
| Ia.287 | —OCH$_2$—CO—N(CH$_3$)—CH$_2$—CO—OCH$_2$—CH$_2$—C$_2$H$_5$ |
| Ia.288 | —OCH$_2$—CO—N(CH$_3$)—CH(CH$_3$)—CO—OH |
| Ia.289 | —OCH$_2$—CO—N(CH$_3$)—CH(CH$_3$)—CO—OCH$_3$ |
| Ia.290 | —OCH$_2$—CO—N(CH$_3$)—CH(CH$_3$)—CO—OC$_2$H$_5$ |
| Ia.291 | —OCH$_2$—CO—N(CH$_3$)—CH(CH$_3$)—CO—OCH$_2$—C$_2$H$_5$ |
| Ia.292 | —OCH$_2$—CO—N(CH$_3$)—CH(CH$_3$)—CO—OCH$_2$—CH$_2$—C$_2$H$_5$ |
| Ia.293 | —OCH(CH$_3$)—CO—NH$_2$ |
| Ia.294 | —OCH(CH$_3$)—CO—NH—CH$_3$ |
| Ia.295 | —OCH(CH$_3$)—CO—N(CH$_3$)$_2$ |
| Ia.296 | —OCH(CH$_3$)—CO—NH—CH$_2$—CO—OH |
| Ia.297 | —OCH(CH$_3$)—CO—NH—CH$_2$—CO—OCH$_3$ |
| Ia.298 | —OCH(CH$_3$)—CO—NH—CH$_2$—CO—OC$_2$H$_5$ |
| Ia.299 | —OCH(CH$_3$)—CO—NH—CH$_2$—CO—OCH$_2$—C$_2$H$_5$ |
| Ia.300 | —OCH(CH$_3$)—CO—NH—CH$_2$—CO—OCH$_2$—CH$_2$—C$_2$H$_5$ |
| Ia.301 | —OCH(CH$_3$)—CO—NH—CH(CH$_3$)—CO—OH |
| Ia.302 | —OCH(CH$_3$)—CO—NH—CH(CH$_3$)—CO—OCH$_3$ |
| Ia.303 | —OCH(CH$_3$)—CO—NH—CH(CH$_3$)—CO—OC$_2$H$_5$ |
| Ia.304 | —OCH(CH$_3$)—CO—NH—CH(CH$_3$)—CO—OCH$_2$—C$_2$H$_5$ |
| Ia.305 | —OCH(CH$_3$)—CO—NH—CH(CH$_3$)—CO—OCH$_2$—CH$_2$—C$_2$H$_5$ |
| Ia.306 | —OCH(CH$_3$)—CO—N(CH$_3$)—CH$_2$—CO—OH |
| Ia.307 | —OCH(CH$_3$)—CO—N(CH$_3$)—CH$_2$—CO—OCH$_3$ |
| Ia.308 | —OCH(CH$_3$)—CO—N(CH$_3$)—CH$_2$—CO—OC$_2$H$_5$ |
| Ia.309 | —OCH(CH$_3$)—CO—N(CH$_3$)—CH$_2$—CO—OCH$_2$—C$_2$H$_5$ |
| Ia.310 | —OCH(CH$_3$)—CO—N(CH$_3$)—CH$_2$—CO—OCH$_2$—CH$_2$—C$_2$H$_5$ |
| Ia.311 | —OCH(CH$_3$)—CO—N(CH$_3$)—CH(CH$_3$)—CO—OH |
| Ia.312 | —OCH(CH$_3$)—CO—N(CH$_3$)—CH(CH$_3$)—CO—OCH$_3$ |
| Ia.313 | —OCH(CH$_3$)—CO—N(CH$_3$)—CH(CH$_3$)—CO—OC$_2$H$_5$ |
| Ia.314 | —OCH(CH$_3$)—CO—N(CH$_3$)—CH(CH$_3$)—CO—OCH$_2$—C$_2$H$_5$ |
| Ia.315 | —OCH(CH$_3$)—CO—N(CH$_3$)—CH(CH$_3$)—CO—OCH$_2$—CH$_2$—C$_2$H$_5$ |
| Ia.316 | —SCH$_2$—CO—NH$_2$ |
| Ia.317 | —SCH$_2$—CO—NH—CH$_3$ |
| Ia.318 | —SCH$_2$—CO—N(CH$_3$)$_2$ |
| Ia.319 | —SCH$_2$—CO—NH—CH$_2$—CO—OH |
| Ia.320 | —SCH$_2$—CO—NH—CH$_2$—CO—OCH$_3$ |

TABLE 1-continued

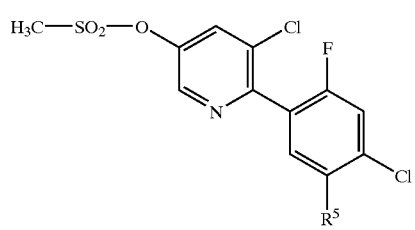

| No. | R⁵ |
|---|---|
| Ia.321 | —SCH$_2$—CO—NH—CH$_2$—CO—OC$_2$H$_5$ |
| Ia.322 | —SCH$_2$—CO—NH—CH$_2$—CO—OCH$_2$—C$_2$H$_5$ |
| Ia.323 | —SCH$_2$—CO—NH—CH$_2$—CO—OCH$_2$—CH$_2$—C$_2$H$_5$ |
| Ia.324 | —SCH$_2$—CO—NH—CH(CH$_3$)—CO—OH |
| Ia.325 | —SCH$_2$—CO—NH—CH(CH$_3$)—CO—OCH$_3$ |
| Ia.326 | —SCH$_2$—CO—NH—CH(CH$_3$)—CO—OC$_2$H$_5$ |
| Ia.327 | —SCH$_2$—CO—NH—CH(CH$_3$)—CO—OCH$_2$—C$_2$H$_5$ |
| Ia.328 | —SCH$_2$—CO—NH—CH(CH$_3$)—CO—OCH$_2$—CH$_2$—C$_2$H$_5$ |
| Ia.329 | —SCH$_2$—CO—N(CH$_3$)—CH$_2$—CO—OH |
| Ia.330 | —SCH$_2$—CO—N(CH$_3$)—CH$_2$—CO—OCH$_3$ |
| Ia.331 | —SCH$_2$—CO—N(CH$_3$)—CH$_2$—CO—OC$_2$H$_5$ |
| Ia.332 | —SCH$_2$—CO—N(CH$_3$)—CH$_2$—CO—OCH$_2$—C$_2$H$_5$ |
| Ia.333 | —SCH$_2$—CO—N(CH$_3$)—CH$_2$—CO—OCH$_2$—CH$_2$—C$_2$H$_5$ |
| Ia.334 | —SCH$_2$—CO—N(CH$_3$)—CH(CH$_3$)—CO—OH |
| Ia.335 | —SCH$_2$—CO—N(CH$_3$)—CH(CH$_3$)—CO—OCH$_3$ |
| Ia.336 | —SCH$_2$—CO—N(CH$_3$)—CH(CH$_3$)—CO—OC$_2$H$_5$ |
| Ia.337 | —SCH$_2$—CO—N(CH$_3$)—CH(CH$_3$)—CO—OCH$_2$—C$_2$H$_5$ |
| Ia.338 | —SCH$_2$—CO—N(CH$_3$)—CH(CH$_3$)—CO—OCH$_2$—CH$_2$—C$_2$H$_5$ |
| Ia.339 | —SCH(CH$_3$)—CO—NH$_2$ |
| Ia.340 | —SCH(CH$_3$)—CO—NH—CH$_3$ |
| Ia.341 | —SCH(CH$_3$)—CO—N(CH$_3$)$_2$ |
| Ia.342 | —SCH(CH$_3$)—CO—NH—CH$_2$—CO—OH |
| Ia.343 | —SCH(CH$_3$)—CO—NH—CH$_2$—CO—OCH$_3$ |
| Ia.344 | —SCH(CH$_3$)—CO—NH—CH$_2$—CO—OC$_2$H$_5$ |
| Ia.345 | —SCH(CH$_3$)—CO—NH—CH$_2$—CO—OCH$_2$—C$_2$H$_5$ |
| Ia.346 | —SCH(CH$_3$)—CO—NH—CH$_2$—CO—OCH$_2$—CH$_2$—C$_2$H$_5$ |
| Ia.347 | —SCH(CH$_3$)—CO—NH—CH(CH$_3$)—CO—OH |
| Ia.348 | —SCH(CH$_3$)—CO—NH—CH(CH$_3$)—CO—OCH$_3$ |
| Ia.349 | —SCH(CH$_3$)—CO—NH—CH(CH$_3$)—CO—OC$_2$H$_5$ |
| Ia.350 | —SCH(CH$_3$)—CO—NH—CH(CH$_3$)—CO—OCH$_2$—C$_2$H$_5$ |
| Ia.351 | —SCH(CH$_3$)—CO—NH—CH(CH$_3$)—CO—OCH$_2$—CH$_2$—C$_2$H$_5$ |
| Ia.352 | —SCH(CH$_3$)—CO—N(CH$_3$)—CH$_2$—CO—OH |
| Ia.353 | —SCH(CH$_3$)—CO—N(CH$_3$)—CH$_2$—CO—OCH$_3$ |
| Ia.354 | —SCH(CH$_3$)—CO—N(CH$_3$)—CH$_2$—CO—OC$_2$H$_5$ |
| Ia.355 | —SCH(CH$_3$)—CO—N(CH$_3$)—CH$_2$—CO—OCH$_2$—C$_2$H$_5$ |
| Ia.356 | —SCH(CH$_3$)—CO—N(CH$_3$)—CH$_2$—CO—OCH$_2$—CH$_2$—C$_2$H$_5$ |
| Ia.357 | —SCH(CH$_3$)—CO—N(CH$_3$)—CH(CH$_3$)—CO—OH |
| Ia.358 | —SCH(CH$_3$)—CO—N(CH$_3$)—CH(CH$_3$)—CO—OCH$_3$ |
| Ia.359 | —SCH(CH$_3$)—CO—N(CH$_3$)—CH(CH$_3$)—CO—OC$_2$H$_5$ |
| Ia.360 | —SCH(CH$_3$)—CO—N(CH$_3$)—CH(CH$_3$)—CO—OCH$_2$—C$_2$H$_5$ |
| Ia.361 | —SCH(CH$_3$)—CO—N(CH$_3$)—CH(CH$_3$)—CO—OCH$_2$—CH$_2$—C$_2$H$_5$ |
| Ia.362 | —OH |
| Ia.363 | —OCH$_3$ |
| Ia.364 | —OC$_2$H$_5$ |
| Ia.365 | —OCH$_2$—C$_2$H$_5$ |
| Ia.366 | —OCH(CH$_3$)$_2$ |
| Ia.367 | —OCH$_2$—CH$_2$—C$_2$H$_5$ |
| Ia.368 | —OCH(CH$_3$)—C$_2$H$_5$ |
| Ia.369 | —OCH$_2$—CH(CH$_3$)$_2$ |
| Ia.370 | —OCH$_2$—CH$_2$—CH$_2$—C$_2$H$_5$ |
| Ia.371 | —OCH$_2$—CH$_2$—CH(CH$_3$)—CH$_3$ |
| Ia.372 | —OCH$_2$—CF$_3$ |
| Ia.373 | —OCHF$_2$ |
| Ia.374 | —OCH$_2$—CH=CH$_2$ |
| Ia.375 | —OCH$_2$—CH=CH—CH$_3$ |
| Ia.376 | —OCH$_2$—CH(CH$_3$)=CH$_2$ |
| Ia.377 | —OCH(CH$_3$)—CH=CH$_2$ |
| Ia.378 | —OCH$_2$—CH=CH—C$_2$H$_5$ |
| Ia.379 | —OCH$_2$—CH$_2$—CH=CH—CH$_3$ |
| Ia.380 | —OCH$_2$—CH$_2$—CH$_2$—CH=CH$_2$ |
| Ia.381 | —OCH$_2$—C≡CH |
| Ia.382 | —OCH(CH$_3$)—C≡CH |
| Ia.383 | —OCH$_2$—C≡C—CH$_3$ |
| Ia.384 | —OCH$_2$—C≡C—C$_2$H$_5$ |

TABLE 1-continued

Ia

Structure: 3-chloro-2-(2-fluoro-4-chloro-5-R⁵-phenyl)-5-(methylsulfonyloxy)pyridine

| No. | R⁵ |
|---|---|
| Ia.385 | Cyclopropyloxy |
| Ia.386 | Cyclobutyloxy |
| Ia.387 | Cyclopentyloxy |
| Ia.388 | Cyclohexyloxy |
| Ia.389 | —OCH$_2$—CH$_2$—OCH$_3$ |
| Ia.390 | —OCH$_2$—CH$_2$—OC$_2$H$_5$ |
| Ia.391 | —OCH$_2$—CH$_2$—OCH$_2$—C$_2$H$_5$ |
| Ia.392 | —OCH$_2$—CH$_2$—OCH(CH$_3$)$_2$ |
| Ia.393 | —SH |
| Ia.394 | —SCH$_3$ |
| Ia.395 | —SC$_2$H$_5$ |
| Ia.396 | —SCH$_2$—C$_2$H$_5$ |
| Ia.397 | —SCH(CH$_3$)$_2$ |
| Ia.398 | —SCH$_2$—CH$_2$—C$_2$H$_5$ |
| Ia.399 | —SCH(CH$_3$)—C$_2$H$_5$ |
| Ia.400 | —SCH$_2$—CH(CH$_3$)$_2$ |
| Ia.401 | —SCH$_2$—CH$_2$—CH$_2$—C$_2$H$_5$ |
| Ia.402 | —SCH$_2$—CH$_2$—CH(CH$_3$)—CH$_3$ |
| Ia.403 | —SCH$_2$—CF$_3$ |
| Ia.404 | —SCHF$_2$ |
| Ia.405 | —SCH$_2$—CH=CH$_2$ |
| Ia.406 | —SCH$_2$—CH=CH—CH$_3$ |
| Ia.407 | —SCH$_2$—CH(CH$_3$)=CH$_2$ |
| Ia.408 | —SCH(CH$_3$)—CH=CH$_2$ |
| Ia.409 | —SCH$_2$—CH=CH—C$_2$H$_5$ |
| Ia.410 | —SCH$_2$—CH$_2$—CH=CH—CH$_3$ |
| Ia.411 | —SCH$_2$—CH$_2$—CH$_2$—CH=CH$_2$ |
| Ia.412 | —SCH$_2$—C≡CH |
| Ia.413 | —SCH(CH$_3$)—C≡CH |
| Ia.414 | —SCH$_2$—C≡C—CH$_3$ |
| Ia.415 | —SCH$_2$—C≡C—C$_2$H$_5$ |
| Ia.416 | Cyclopropylthio |
| Ia.417 | Cyclobutylthio |
| Ia.418 | Cyclopentylthio |
| Ia.419 | Cyclohexylthio |
| Ia.420 | —SCH$_2$—CH$_2$—OCH$_3$ |
| Ia.421 | —SCH$_2$—CH$_2$—OC$_2$H$_5$ |
| Ia.422 | —SCH$_2$—CH$_2$—OCH$_2$—C$_2$H$_5$ |
| Ia.423 | —SCH$_2$—CH$_2$—OCH(CH$_3$)$_2$ |
| Ia.424 | —CH=CH$_2$—CO—OH |
| Ia.425 | —CH=CH$_2$—CO—OCH$_3$ |
| Ia.426 | —CH=CH$_2$—CO—OC$_2$H$_5$ |
| Ia.427 | —CH=CH$_2$—CO—OCH$_2$—C$_2$H$_5$ |
| Ia.428 | —CH=CH$_2$—CO—OCH$_2$—CH$_2$—C$_2$H$_5$ |
| Ia.429 | —CH=CH(Cl)—CO—OH |
| Ia.430 | —CH=CH(Cl)—CO—OCH$_3$ |
| Ia.431 | —CH=CH(Cl)—CO—OC$_2$H$_5$ |
| Ia.432 | —CH=CH(Cl)—CO—OCH$_2$—C$_2$H$_5$ |
| Ia.433 | —CH=CH(Cl)—CO—OCH$_2$—CH$_2$—C$_2$H$_5$ |
| Ia.434 | —CH=CH(CH$_3$)—CO—OH |
| Ia.435 | —CH=CH(CH$_3$)—CO—OCH$_3$ |
| Ia.436 | —CH=CH(CH$_3$)—CO—OC$_2$H$_5$ |
| Ia.437 | —CH=CH(CH$_3$)—CO—OCH$_2$—C$_2$H$_5$ |
| Ia.438 | —CH=CH(CH$_3$)—CO—OCH$_2$—CH$_2$—C$_2$H$_5$ |
| Ia.439 | —CH=CH—CO—NH$_2$ |
| Ia.440 | —CH=CH—CO—NH—CH$_3$ |
| Ia.441 | —CH=CH—CO—N(CH$_3$)$_2$ |
| Ia.442 | —CH=CH—CO—NH—CH$_2$—CO—OH |
| Ia.443 | —CH=CH—CO—NH—CH$_2$—CO—OCH$_3$ |
| Ia.444 | —CH=CH—CO—NH—CH$_2$—CO—OC$_2$H$_5$ |
| Ia.445 | —CH=CH—CO—NH—CH(CH$_3$)—CO—OH |
| Ia.446 | —CH=CH—CO—NH—CH(CH$_3$)—CO—OCH$_3$ |
| Ia.447 | —CH=CH—CO—NH—CH(CH$_3$)—CO—OC$_2$H$_5$ |
| Ia.448 | —CH=CH—CO—N(CH$_3$)—CH$_2$—CO—OH |

TABLE 1-continued

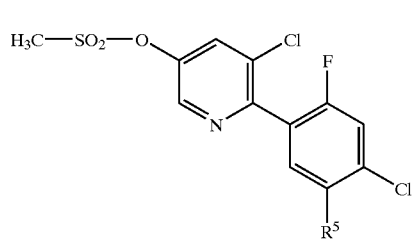

| No. | R⁵ |
|---|---|
| Ia.449 | —CH=CH—CO—N(CH₃)—CH₂—CO—OCH₃ |
| Ia.450 | —CH=CH—CO—N(CH₃)—CH₂—CO—OC₂H₅ |
| Ia.451 | —CH=CH—CO—N(CH₃)—CH(CH₃)—CO—OH |
| Ia.452 | —CH=CH—CO—N(CH₃)—CH(CH₃)—CO—OCH₃ |
| Ia.453 | —CH=CH—CO—N(CH₃)—CH(CH₃)—CO—OC₂H₅ |
| Ia.454 | —CH=C(Cl)—CO—NH—CH(CH₃)—CO—OH |
| Ia.455 | —CH=C(Cl)—CO—NH—CH(CH₃)—CO—OCH₃ |
| Ia.456 | —CH=C(Cl)—CO—NH—CH(CH₃)—CO—OC₂H₅ |
| Ia.457 | —CH=C(Cl)—CO—N(CH₃)—CH₂—CO—OH |
| Ia.458 | —CH=C(Cl)—CO—N(CH₃)—CH₂—CO—OCH₃ |
| Ia.459 | —CH=C(Cl)—CO—N(CH₃)—CH₂—CO—OC₂H₅ |
| Ia.460 | —CH=C(Cl)—CO—N(CH₃)—CH(CH₃)—CO—OH |
| Ia.461 | —CH=C(Cl)—CO—N(CH₃)—CH(CH₃)—CO—OCH₃ |
| Ia.462 | —CH=C(Cl)—CO—N(CH₃)—CH(CH₃)—CO—OC₂H₅ |
| Ia.463 | —CHO |
| Ia.464 | —CO—CH₃ |
| Ia.465 | —CO—C₂H₅ |
| Ia.466 | —CO—CH₂—C₂H₅ |
| Ia.467 | —CO—CH(CH₃)₂ |
| Ia.468 | —CO—CH₂—CH₂—C₂H₅ |
| Ia.469 | —CO—CH₂—CH(CH₃)—CH₃ |
| Ia.470 | —CO—CH(CH₃)—C₂H₅ |
| Ia.471 | —CO—CH₂—Cl |
| Ia.472 | —CO—CH₂—Br |
| Ia.473 | —CO—CHCl₂ |
| Ia.474 | —CO—CHBr₂ |
| Ia.475 | —CO—CCl₃ |
| Ia.476 | —CO—CF₃ |
| Ia.477 | —CH=C(CH₃)—CO—NH₂ |
| Ia.478 | —CH=C(CH₃)—CO—NH—CH₃ |
| Ia.479 | —CH=C(CH₃)—CO—N(CH₃)₂ |
| Ia.480 | —CH=C(CH₃)—CO—NH—CH₂—CO—OH |
| Ia.481 | —CH=C(CH₃)—CO—NH—CH₂—CO—OCH₃ |
| Ia.482 | —CH=C(CH₃)—CO—NH—CH₂—CO—OC₂H₅ |
| Ia.483 | —CH=C(CH₃)—CO—NH—CH(CH₃)—CO—OH |
| Ia.484 | —CH=C(CH₃)—CO—NH—CH(CH₃)—CO—OCH₃ |
| Ia.485 | —CH=C(CH₃)—CO—NH—CH(CH₃)—CO—OC₂H₅ |
| Ia.486 | —CH=C(CH₃)—CO—N(CH₃)—CH₂—CO—OH |
| Ia.487 | —CH=C(CH₃)—CO—N(CH₃)—CH₂—CO—OCH₃ |
| Ia.488 | —CH=C(CH₃)—CO—N(CH₃)—CH₂—CO—OC₂H₅ |
| Ia.489 | —CH=C(CH₃)—CO—N(CH₃)—CH(CH₃)—CO—OH |
| Ia.490 | —CH=C(CH₃)—CO—N(CH₃)—CH(CH₃)—CO—OCH₃ |
| Ia.491 | —CH=C(CH₃)—CO—N(CH₃)—CH(CH₃)—CO—OC₂H₅ |
| Ia.492 | —CH=C(Cl)—CO—NH₂ |
| Ia.493 | —CH=C(Cl)—CO—NH—CH₃ |
| Ia.494 | —CH=C(Cl)—CO—N(CH₃)₂ |
| Ia.495 | —CH=C(Cl)—CO—NH—CH₂—CO—OH |
| Ia.496 | —CH=C(Cl)—CO—NH—CH₂—CO—OCH₃ |
| Ia.497 | —CH=C(Cl)—CO—NH—CH₂—CO—OC₂H₅ |
| Ia.498 | —CO—CH₂—CH=CH₂ |
| Ia.499 | —CO—CH₂—CH=CH—CH₃ |
| Ia.500 | —CO—CH₂—CH₂—CH=CH₂ |
| Ia.501 | —CO—CH₂—C≡CH |
| Ia.502 | —CO—CH(CH₃)—C≡CH |
| Ia.503 | —CO—CH₂—C≡C—CH₃ |
| Ia.504 | Cyclopropylcarbonyl |
| Ia.505 | Cyclobutylcarbonyl |
| Ia.506 | Cyclopentylcarbonyl |
| Ia.507 | Cyclohexylcarbonyl |
| Ia.508 | —CO—CH₂—OCH₃ |
| Ia.509 | —CO—CH₂—OC₂H₅ |
| Ia.510 | —CO—CH₂—CH₂—OCH₃ |
| Ia.511 | —CO—CH₂—CH₂—OC₂H₅ |
| Ia.512 | 1,3-Dioxolan-2-yl |

TABLE 1-continued

Ia

[Structure: Pyridine ring with H₃C—SO₂—O— at position 5, Cl at position 3, and at position 2 a phenyl group bearing F (ortho), Cl (para to attachment relative to F), and R⁵]

| No. | R⁵ |
|---|---|
| Ia.513 | 4-(CH₃)-1,3-dioxolan-2-yl |
| Ia.514 | 4,5-(CH₃)₂-1,3-dioxolan-2-yl |
| Ia.515 | 4,4-(CH₃)₂-1,3-dioxolan-2-yl |
| Ia.516 | 4,4,5-(CH₃)₃-1,3-dioxolan-2-yl |
| Ia.517 | 4,4,5,5-(CH₃)₄-1,3-dioxolan-2-yl |
| Ia.518 | 4-(COOCH₃)-1,3-dioxolan-2-yl |
| Ia.519 | 4-(COOC₂H₅)-1,3-dioxolan-2-yl |
| Ia.520 | 4-(COOCH₂C₂H₅)-1,3-dioxolan-2-yl |
| Ia.521 | 4-[COOCH(CH₃)₂]-1,3-dioxolan-2-yl |
| Ia.522 | 4-(COOCH₂—C₂H₅)-1,3-dioxolan-2-yl |
| Ia.523 | 4-[COOCH₂CH(CH₃)₂]-1,3-dioxolan-2-yl |
| Ia.524 | 4-[COOCH(CH₃)C₂H₅]-1,3-dioxolan-2-yl |
| Ia.525 | 4-[COOC(CH₃)₃]-1,3-dioxolan-2-yl |
| Ia.526 | 4,5-(COOCH₃)₂-1,3-dioxolan-2-yl |
| Ia.527 | 4,5-(COOC₂H₅)₂-1,3-dioxolan-2-yl |
| Ia.528 | [Structure: 1,3-oxathiolan-2-yl] |
| Ia.529 | 1,3-Dithiolan-2-yl |
| Ia.530 | 4-(CH₃)-1,3-dithiolan-2-yl |
| Ia.531 | 4,5-(CH₃)₂-1,3-dithiolan-2-yl |
| Ia.532 | 4,4-(CH₃)₂-1,3-dithiolan-2-yl |
| Ia.533 | 4-(COOCH₃)-1,3-dithiolan-2-yl |
| Ia.534 | 4-(COOC₂H₅)-1,3-dithiolan-2-yl |
| Ia.535 | 4-(COOCH₂C₂H₅)-1,3-dithiolan-2-yl |
| Ia.536 | 4-[COOCH(CH₃)₂]-1,3-dithiolan-2-yl |
| Ia.537 | 4-(COOCH₂CH₂C₂H₅)-1,3-dithiolan-2-yl |
| Ia.538 | 4-[COOCH₂CH(CH₃)₂]-1,3-dithiolan-2-yl |
| Ia.539 | 4-[COOCH(CH₃)C₂H₅]-1,3-dithiolan-2-yl |
| Ia.540 | 4-[COOC(CH₃)₃]-1,3-dithiolan-2-yl |
| Ia.541 | 4,5-(COOCH₃)₂-1,3-dithiolan-2-yl |
| Ia.542 | 4,5-(COOC₂H₅)₂-1,3-dithiolan-2-yl |
| Ia.543 | —CH=N—OH |
| Ia.544 | —CH=N—OCH₃ |
| Ia.545 | —CH=N—OC₂H₅ |
| Ia.546 | —CH=N—OCH₂—C₂H₅ |
| Ia.547 | —CH=N—OCH(CH₃)₂ |
| Ia.548 | —CH=N—OCH₂—CH₂—C₂H₅ |
| Ia.549 | —CH=N—OCH₂—CH(CH₃)₂ |
| Ia.550 | —CH=N—OCH(CH₃)—C₂H₅ |
| Ia.551 | —CH=N—OC(CH₃)₃ |
| Ia.552 | —CH=N—OCH₂—CH₂—CH₂—C₂H₅ |
| Ia.553 | —CH=N—OCH₂—CH₂—CH(CH₃)₂ |
| Ia.554 | —CH=N—OCH₂—CO—OCH₃ |
| Ia.555 | —CH=N—OCH₂—CO—OC₂H₅ |
| Ia.556 | —CH=N—OCH₂—CO—OCH₂—C₂H₅ |
| Ia.557 | —CH=N—OCH(CH₃)—CO—OCH₃ |
| Ia.558 | —CH=N—OCH(CH₃)—CO—OC₂H₅ |
| Ia.559 | —CH=N—OCH(CH₃)—CO—OCH₂—C₂H₅ |
| Ia.560 | —CH(OCH₃)₂ |
| Ia.561 | —CH(OC₂H₅)₂ |
| Ia.562 | —CH(OCH₂—C₂H₅)₂ |
| Ia.563 | —CH(OCH₂—CH₂—C₂H₅)₂ |
| Ia.564 | —NO₂ |
| Ia.565 | —NH—OH |
| Ia.566 | —NH₂ |
| Ia.567 | —NH—CH₃ |
| Ia.568 | —N(CH₃)₂ |
| Ia.569 | —NH—CH₂—CO—OCH₃ |
| Ia.570 | —NH—CH₂—CO—OC₂H₅ |
| Ia.571 | —NH—CH₂—CO—OCH₂—C₂H₅ |

TABLE 1-continued

Ia (structure: 3-chloro-2-(4-chloro-2-fluoro-5-R⁵-phenyl)-5-(methylsulfonyloxy)pyridine)

| No. | R⁵ |
|---|---|
| Ia.572 | —NH—CH₂—CO—OCH₂—CH₂—C₂H₅ |
| Ia.573 | —NH—CH(CH₃)—CO—OCH₃ |
| Ia.574 | —NH—CH(CH₃)—CO—OC₂H₅ |
| Ia.575 | —NH—CH(CH₃)—CO—OCH₂—C₂H₅ |
| Ia.576 | —NH—CH(CH₃)—CO—OCH₂—CH₂—C₂H₅ |
| Ia.577 | —N(CH₃)—CH₂—CO—OCH₃ |
| Ia.578 | —N(CH₃)—CH₂—CO—OC₂H₅ |
| Ia.579 | —N(CH₃)—CH₂—CO—OCH₂—C₂H₅ |
| Ia.580 | —N(CH₃)—CH₂—CO—OCH₂—CH₂—C₂H₅ |
| Ia.581 | —N(CH₃)—CH(CH₃)—CO—OCH₃ |
| Ia.582 | —N(CH₃)—CH(CH₃)—CO—OC₂H₅ |
| Ia.583 | —N(CH₃)—CH(CH₃)—CO—OCH₂—C₂H₅ |
| Ia.584 | —N(CH₃)—CH(CH₃)—CO—OCH₂—CH₂—C₂H₅ |
| Ia.585 | —NH—SO₂—CH₃ |
| Ia.586 | —NH—SO₂—C₂H₅ |
| Ia.587 | —NH—SO₂—CH₂—C₂H₅ |
| Ia.588 | —NH—SO₂—CH(CH₃)₂ |
| Ia.589 | —NH—SO₂—CH₂—CH₂—C₂H₅ |
| Ia.590 | —NH—SO₂—CH₂—CH(CH₃)₂ |
| Ia.591 | —NH—SO₂—CH(CH₃)—C₂H₅ |
| Ia.592 | —N(CH₃)—SO₂—CH₃ |
| Ia.593 | —N(CH₃)—SO₂—C₂H₅ |
| Ia.594 | —N(CH₃)—SO₂—CH₂—C₂H₅ |
| Ia.595 | —N(CH₃)—SO₂—CH(CH₃)₂ |
| Ia.596 | —N(CH₃)—SO₂—CH₂—CH₂—C₂H₅ |
| Ia.597 | —N(CH₃)—SO₂—CH₂—CH(CH₃)₂ |
| Ia.598 | —NH—CO—CH₃ |
| Ia.599 | —NH—CO—C₂H₅ |
| Ia.600 | —NH—CO—CH₂—C₂H₅ |
| Ia.601 | —NH—CO—CH(CH₃)₂ |
| Ia.602 | —NH—CO—CH₂—CH₂—C₂H₅ |
| Ia.603 | —NH—CO—CH₂—CH(CH₃)₂ |
| Ia.604 | —NH—CO—CH(CH₃)—C₂H₅ |
| Ia.605 | —NH—CO—C(CH₃)₃ |
| Ia.606 | —N(CH₃)—CO—CH₃ |
| Ia.607 | —N(CH₃)—CO—C₂H₅ |
| Ia.608 | —N(CH₃)—CO—CH₂—C₂H₅ |
| Ia.609 | —N(CH₃)—CO—CH(CH₃)₂ |
| Ia.610 | —N(CH₃)—CO—CH₂—CH₂—C₂H₅ |
| Ia.611 | —N(CH₃)—CO—CH₂—CH(CH₃)₂ |
| Ia.612 | —N(CH₃)—CO—CH(CH₃)—C₂H₅ |
| Ia.613 | —N(CH₃)—CO—C(CH₃)₃ |
| Ia.614 | —SO₂—Cl |
| Ia.615 | —SO₂—OH |
| Ia.616 | —SO₂—NH₂ |
| Ia.617 | —SO₂—NH—CH₃ |
| Ia.618 | —SO₂—N(CH₃)₂ |
| Ia.619 | —SO₂—NH—CH₂—CO—OCH₃ |
| Ia.620 | —SO₂—NH—CH₂—CO—OC₂H₅ |
| Ia.621 | —SO₂—NH—CH(CH₃)—CO—OCH₃ |
| Ia.622 | —SO₂—NH—CH(CH₃)—CO—OC₂H₅ |
| Ia.623 | —SO₂—N(CH₃)—CH₂—CO—OCH₃ |
| Ia.624 | —SO₂—N(CH₃)—CH₂—CO—OC₂H₅ |
| Ia.625 | —SO₂—N(CH₃)—CH(CH₃)—CO—OCH₃ |
| Ia.626 | —SO₂—N(CH₃)—CH(CH₃)—CO—OC₂H₅ |
| Ia.627 | 1,3-Dioxan-2-yl |
| Ia.628 | 4-(CH₃)-1,3-dioxan-2-yl |
| Ia.629 | 5-(CH₃)-1,3-dioxan-2-yl |
| Ia.630 | 5,5-(CH₃)₂-1,3-dioxan-2-yl |
| Ia.631 | (1,3-oxathian-2-yl) |

TABLE 1-continued

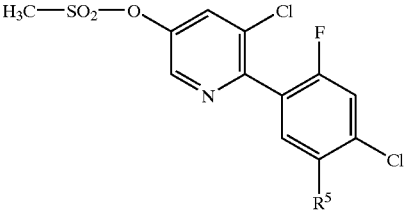

| No. | R⁵ |
|---|---|
| Ia.632 | 1,3-Dithian-2-yl |
| Ia.633 | 4-(CH₃)-dithian-2-yl |
| Ia.634 | 5-(CH₃)-dithian-2-yl |
| Ia.635 | 5,5-(CH₃)₂-dithian-2-yl |
| Ia.636 | OCH(CH₃)—CO—OCH₂—CH₂—OCH₃ |
| Ia.637 | OCH(CH₃)—CO—OCH₂—CH=CH₂ |

Furthermore, very particular preference is given to the substituted 2-phenylpyridines of the formulae Ib, Ic, Id, Ie and If, in particular to the compounds Ib.1 to Ib.637, which differ from the corresponding compounds Ia.1 to Ia.637 only in that $R^3$ is chlorine:

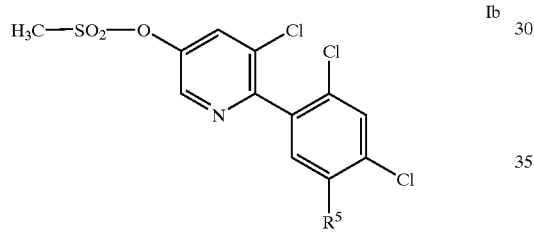

the compounds Ic.1 to Ic.637, which differ from the corresponding compounds Ia.1 to Ia.637 only in that $R^3$ is hydrogen:

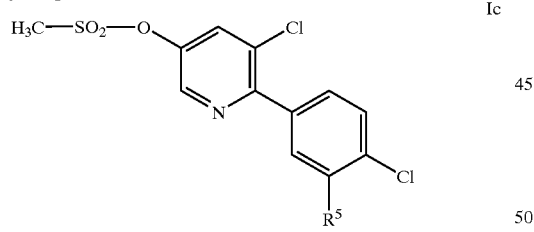

the compounds Id.1 to Id.637, which differ from the corresponding compounds Ia.1 to Ia.637 only in that $R^4$ is cyano:

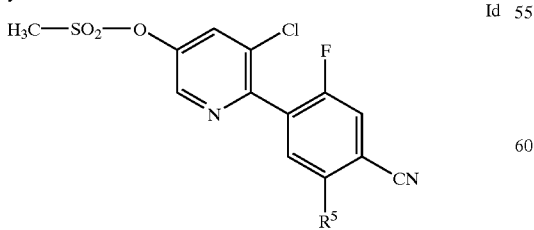

the compounds Ie.1 to Ie.637, which differ from the corresponding compounds Ia.1 to Ia.637 only in that $R^3$ is chlorine and $R^4$ is cyano:

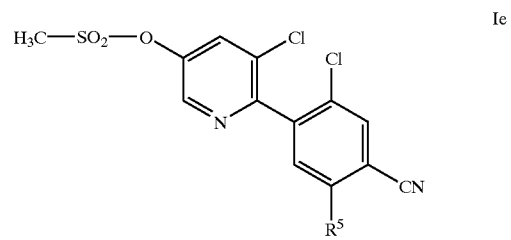

the compounds If.1 to If.637, which differ from the corresponding compounds Ia.1 to Ia.637 only in that $R^3$ is hydrogen and $R^4$ is cyano:

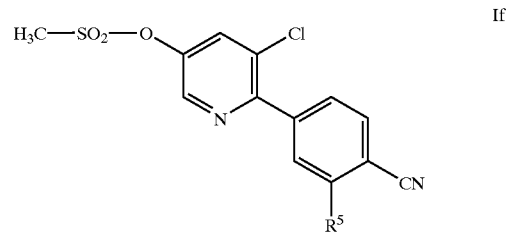

The substituted 2-phenylpyridines of the formula I can be obtained by different routes, for example by one of the following processes:

Process A)

Oxidation of substituted 2-phenylpyridines of the formula I where n is zero and $R^1$ and $R^5$ do not contain any oxidizable sulfur, in the manner known per se {cf., for example, A. Albini & S. Pietra, Heterocyclic N—Oxides, CRC-Press Inc., Boca Raton, USA 1991; H. S. Mosher et al., Org. Synth. Coll. Vol. IV 1963, page 828; E. C. Taylor et al., Org. Synth. Coll. Vol. IV 1963, page 704; T. W. Bell et. al., Org. Synth. 69, page 226 (1990)}:

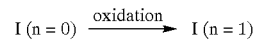

Among the oxidizing agents which are customary for oxidizing the pyridine ring, peracetic acid, trifluoroperacetic acid, perbenzoic acid, m-chloroperbenzoic acid, monopermaleic acid, magnesium monoperphthalate, sodium perborate, oxone® (contains peroxydisulfate) pertungstic acid and hydrogen peroxide may be mentioned by way of example.

Suitable solvents are, for example, water, sulfuric acid, carboxylic acids, such as acetic acid and trifluoroacetic acid, and also halogenated hydrocarbons, such as dichloromethane and chloroform.

The oxidation usually succeeds at temperatures from 0° C. to the boiling point of the reaction mixture.

The oxidizing agent is usually employed in at least equimolar amounts, based on the starting material. In general, an excess of oxidizing agent has been found to be particularly advantageous.

Process B)

Transition-metal-catalyzed crosscoupling reaction of 2-halopyridines II (Hal=chlorine or bromine) with organometallic compounds of the formula III in the manner known per se {cf., for example, WO 95/02580 and the literature cited therein on pages 21 and 22}:

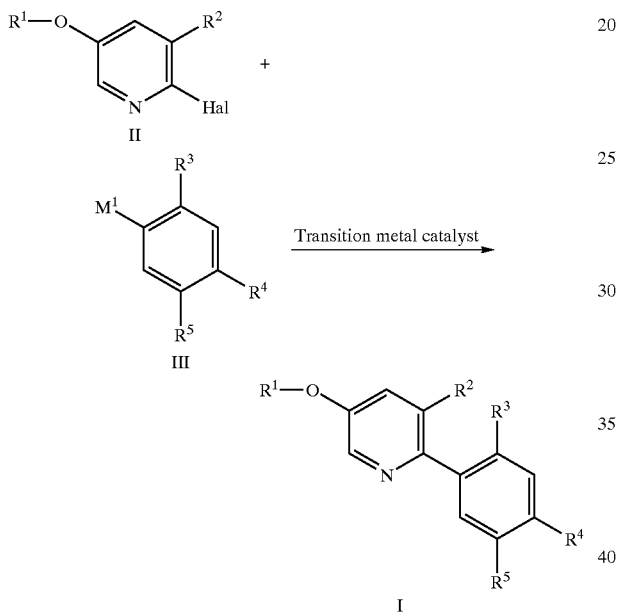

$M^1$ is $B(OH)_2$, Mg—Cl, Mg—Br, Mg—I, Zn—Cl, Zn—Br, Zn—I, lithium, copper or tri($C_1$–$C_4$-alkyl)tin, preferably $B(OH)_2$, Mg—Cl, Mg—Br, Mg—I, Zn—Cl, Zn—Br or Zn—I.

Alternatively, instead of the boronic acids III {$M^1$=B(OH)$_2$}, it is also possible to use the boroxines IV:

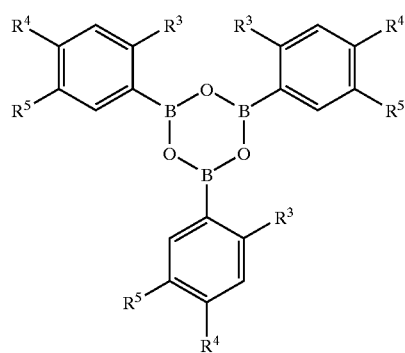

Suitable catalysts are, in particular, palladium catalysts, such as tetrakis(triphenylphosphine)palladium(O), bis(triphenylphosphine)palladium(II) chloride, 1,4-bis(diphenylphosphino)butanepalladium(II) chloride, 1,2-bis(diphenylphosphino)ethanepalladium(II) chloride, palladium(II) acetate+triphenylphosphine, palladium(II) acetate+tri(o-tolyl)phosphine or palladium on activated carbon, and nickel catalysts, such as bis(triphenylphosphine)nickel(II) chloride, 1,3-bis(diphenylphosphino)propanenickel(II) chloride or nickel(II) acetylacetonate.

Process C)

Diazotization of 5-amino-2-phenylpyridines V, reaction of the diazonium salts with acetic anhydride, hydrolysis of VI to give 5-hydroxy-2-phenylpyridine VII and reaction of VII with $R^1$—L, where L is a suitable leaving group, such as chloride (in the case of $R^1$=$C_1$–$C_6$-alkylsulfonyl):

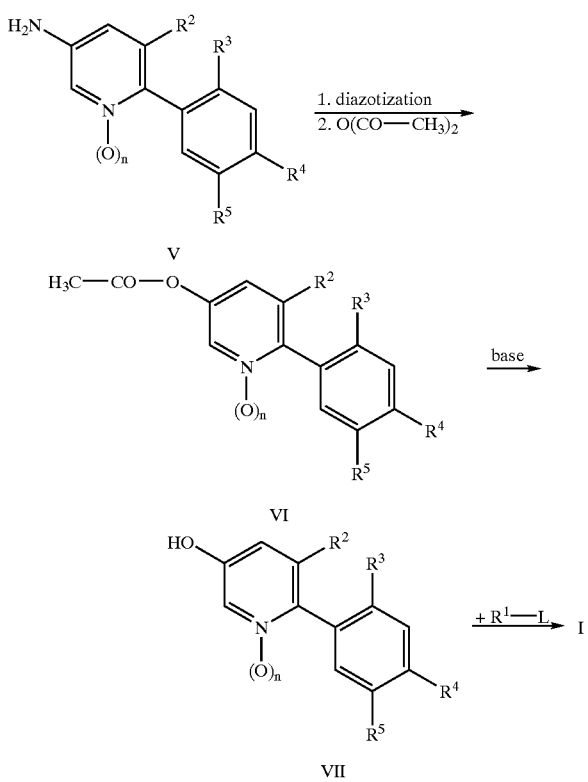

Reactions of this type are generally known, for example from the following publications (diazotization of aminopyridines using isoamylnitrite): C. S. Giam et al., J. Chem. Soc., Chem. Commun. 16, 756 (1980); T. Yasumitsu et al., J. Org. Chem. 46, 3564–3567 (1981).

The 5-amino-2-phenylpyridines of the formula V are known from WO 98/07700 or can be obtained in the manner described therein.

5-Amino-2-(4-chloro-3-methoxyphenyl)pyridine and 5-amino-2-(4-chloro-3-methoxyphenyl)-3-chloropyridine have already been disclosed in WO 95/02580.

Process D)

Reaction of 5-hydroxy-2-phenylpyridines VIII with a $C_1$–$C_6$-alkylsulfinyl chloride $R^1$—SO—Cl in a manner known per se {cf., for example, J. Hendrickson & P. Skipper, Tetrahedron 32, 1627 (1976); Th. Netscher & H. Prinzbach, Synthesis 8, 683–688 (1987); Y. F. Zhang et al., Inorg. Chem. 31, 492–494 (1992), M. Jung & T. Lazarova, Tetrahedron Letters 37, 7–8 (1996)}:

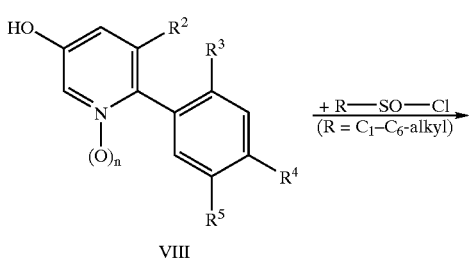

VIII

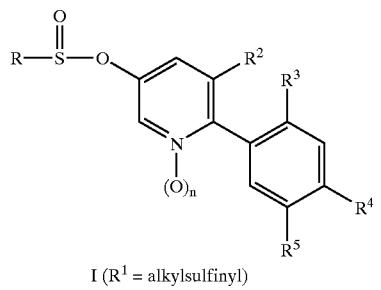

I (R¹ = alkylsulfinyl)

Process E)

Oxidation of substituted 2-phenylpyridines of the formula I in which R¹ is $C_1$–$C_6$-alkylsulfinyl and the substituent R⁵ does not contain any oxidizable sulfur, in a manner known per se {cf., for example, Th. Squires et al., J. Org. Chem. 46, 2373–2376 (1981) and Th. Netscher & H. Prinzbach, Synthesis 8, 683–688 (1987)}:

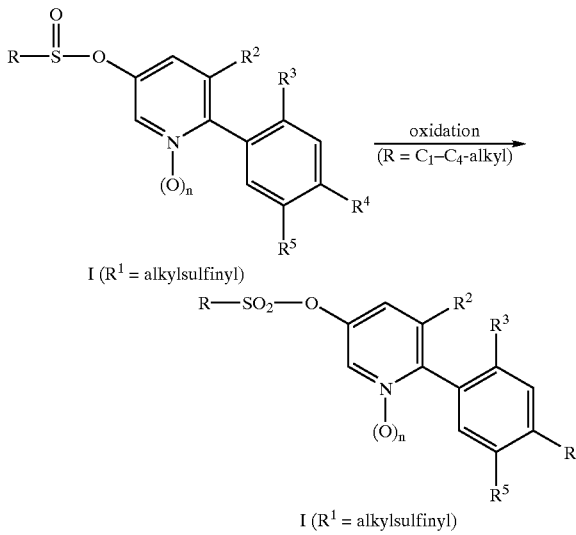

I (R¹ = alkylsulfinyl)

For suitable solvents, reaction temperatures and ratios, reference is made to the details given under Process A). In addition to the oxidizing agents mentioned under Process A), alkali metal hypohalides, such as sodium hypochloride and potassium hydrochloride, are also suitable here.

The substituted 2-phenylpyridines I can usually be prepared by one of the abovementioned synthesis processes. However, for economical or technical reasons, it may be more expedient to prepare some of the compounds I from similar 2-phenylpyridines which differ in the meaning of one radical.

The compounds of the formula IIa

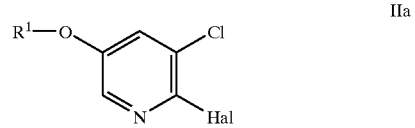

IIa are novel.

In general, the 2-halopyridines II can be prepared, for example, by diazotization of the corresponding 5-aminopyridines IX[1])

[1]) for their preparation, cf. J. Med. Chem 16, 319–327 (1973) —preferably using a nitrite such as tert-butylnitrite and isopentylnitrite—C followed by reaction of the diazonium salt with acetic anhydride analogously to Process C):

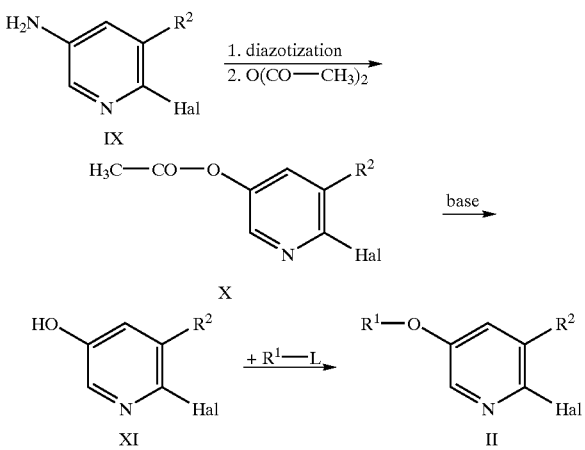

The process is preferably carried out in an anhydrous system, for example in hydrogen chloride-containing glacial acetic acid, in dioxane, absolute ethanol, tetrahydrofuran, acetonitrile or in acetone. The reaction temperature is usually from (−30) to 80° C.

In general, the components of the diazotization reaction are employed in approximately stoichiometric amounts; however, it may also be advantageous to use an excess of one of the components, for example with respect to a conversion of the other component which is as complete as possible. Preference is given to using an excess of nitrite, up to about two times the molar amount, based on the amount of IX.

The acetic anhydride is advantageously employed in approximately equimolar amounts or in excess, based on the diazonium salt. In general, a large excess of acetic anhydride (up to about 100 times the molar amount), based on the amount of diazonium salt, has been found to be particularly advantageous.

The 2-halopyridines II where $R^1=C_1$–$C_6$-alkylsulfinyl can subsequently be oxidized to the corresponding compounds II where $R^1=C_1$–$C_6$-alkylsulfonyl, as described under Process E) for the compounds I where $R^1=C_1$–$C_6$-alkylsulfinyl.

Unless stated otherwise, all the processes described above are advantageously carried out at atmospheric pressure or under the autogenous pressure of the reaction mixture in question.

The work-up of the reaction mixtures is usually carried out in a conventional manner, for example by dilution of the reaction solution with water and subsequent isolation of the product by filtration, crystallization or solvent extraction, or by removing the solvent, partitioning the residue in a mixture of water and a suitable organic solvent and work-up of the organic phase to afford the product.

The substituted 2-phenylpyridines I can be obtained as isomer mixtures in the preparation; however, if desired, these can be separated into largely pure isomers using customary methods such as crystallization or chromatography, including chromatography over an optically active adsorbent. Pure optically active isomers can be prepared advantageously from suitable optically active starting materials.

Agriculturally useful salts of the compounds I can be formed by reaction with a base of the corresponding cation, preferably an alkali metal hydroxide or hydride.

Salts of I where the metal ion is not an alkali metal ion can also be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, for use as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method used in each case, the compounds I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N. rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods. Moreover, the substituted 2-phenylpyridines I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which is made possible by dehiscence, or reduction of the adherence to the tree, both concentrated over a period of time, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee a very fine distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight, of at least one active compound. The active compounds are employed in a purity of from 90% to 100%, preferably 95% to 100% (according to the NMR spectrum).

The formulation examples which follow illustrate the preparation of such products:

I. 20 parts by weight of the compound No. Ia.363 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. Ia.362 are dissolved in a mixture composed of 40 parts by weight of cyclohexanone, 30 parts by weight of isobutanol, 20 parts by weight of the adduct of 7 mol of ethylene oxide to 1 mol of isooctyl-phenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. Ia.374 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. Ia.363 are mixed thoroughly with 3 parts by weight of sodium diisobutyl-naphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. Ia.362 are mixed with 97 parts by weight of finely divided kaolin. This gives a dust which comprises 3% by weight of the active compound.

VI. 20 parts by weight of the active compound No. Ia.374 are mixed intimately with 2 parts by weight of calcium dodecyl benzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ia.363 is dissolved in a mixture composed of 70 parts by weight of cyclohexanone, parts by weight of ethoxylated isooctylphenol and 10 parts by weight of ethoxylated castor oil. This gives a stable emulsion concentrate.

VIII. 1 part by weight of the compound No. Ia.374 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 2-phenylpyridines I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy/ hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitro-anilines, dinitrophenols, diphenyl ethers, dipyridyls, halocarboxylic acids and their derivatives, ureas, 3-phenyl-uracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonyl-ureas, triazines, triazinones, triazolinones, triazolecarbox-amides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

Compound Ia.363 in Table 1

8.5 ml of a 2 molar solution of isopropylmagnesium chloride in tetrahydrofuran were added dropwise to a solution of 3.7 g of 5-bromo-2-chloro-4-fluoroanisole in 80 ml of tetrahydrofuran. After 30 minutes of stirring, the resulting mixture was, at 0° C., added dropwise to a solution of 5.7 g of 3-chloro-5-(methylsulfonyloxy)-2-(phenylsulfonyl) pyridine in 100 ml of tetrahydrofuran. The entire reaction mixture was then stirred at approximately 20° C. for 17 h. The mixture was subsequently heated at reflux temperature for 72 hours. The low-boiling fractions were then distilled off. The residue was taken up in 1 l of ethyl acetate. The organic phase was washed with 2×250 ml of water, dried over magnesium sulfate and finally concentrated. The crude product was purified by silica gel chromatography (mobile phase: ethyl acetate/cyclohexane (1:1)). Yield: 2.9 g.

Intermediate 1.1: 3-Chloro-2-hydroxy-5-nitropyridine

Initially, 190.9 g of 2-hydroxy-5-nitropyridine were dissolved at 50° C. in 650 ml of conc. hydrochloric acid. Over a period of one hour, a solution of 42.9 g of potassium chlorate in 600 ml of water was added dropwise to this mixture. After cooling to approximately 20° C., the mixture was stirred for another 45 minutes and then cooled to 0° C. The solid fraction was subsequently filtered off and suspended in 200 ml of water. The undissolved product was finally filtered off and dried at 50° C. under reduced pressure. Yield: 162.9 g; m.p.: 197–198° C.

Intermediate 1.2: 2,3-Dichloro-5-nitropyridine

At 0° C., 39.9 g of quinoline and, after 5 minutes and a little at a time, 108 g of 3-chloro-2-hydroxy-5-nitropyridine were added to 95 g of phosphorus oxytrichloride. After addition of a further 30 ml of phosphorus oxytrichloride, the mixture was heated at reflux temperature for 2 hours. For work-up, the reaction mixture was cooled to 50–60° C. and stirred into approximately 3 l of ice-water. The mixture was subsequently stirred for another 2 hours, and the resulting solid fraction was then filtered off, washed with 500 ml of water and dried under reduced pressure. Yield: 110.7 g.

Intermediate 1.3: 2,3-Dichloro-5-aminopyridine 1 g of platinum on activated carbon was added to a solution of 67.4 g of 2,3-dichloro-5-nitropyridine in 800 ml of tetrahydrofuran. 25 l of hydrogen were subsequently introduced, and the reaction mixture was, toward the end of the reaction, heated to 50° C. The insoluble components were then filtered off. The filtrate was concentrated. Yield: 56 g.

Intermediate 1.4: 2,3-Dichloro-5-azidopyridine Tetrafluoroborate

At 0° C., a solution of 45.6 g of sodium nitrite in 100 ml of water was added dropwise to a solution of 98 g of 2,3-dichloro-5-aminopyridine in 600 ml of 48% strength tetrafluoroboric acid. After one hour, the resulting solid was filtered off and, in order to prevent sudden decomposition, processed further in a moist state.

Intermediate 1.5: 5-Acetyloxy-2,3-dichloropyridine 42 g of the diazonium salt from intermediate 1.4 and 300 ml of acetic anhydride were heated at reflux temperature for one hour. The mixture was subsequently concentrated. The residue was taken up in 400 ml of diethyl ether, and the solution was washed twice with in each case 200 ml of water, dried over magnesium sulfate and finally reconcentrated. The crude product was purified by silica gel chromatography (mobile phase: ethyl acetate/cyclohexane (1:1)). Yield: 16 g.

Intermediate 1.6: 2,3-Dichloro-5-hydroxypyridine

At 0° C., a solution of 13 g of sodium hydroxide in 80 ml of water was added to 16 g of 5-acetyloxy-2,3-dichloropyridine in 100 ml of ice-water. The mixture was subsequently initially stirred at 0° C. for one hour and then at approximately 20° C. for 17 hours, and the reaction mixture was then washed with 150 ml of ethyl acetate. The mixture was acidified up to a pH of 4–5 by addition of acetic acid and then extracted three times with 100 ml of ethyl acetate each time. The combined organic phases were dried over magnesium sulfate and finally concentrated. Yield: 12.2 g.

Intermediate 1.7: 2,3-Dichloro-5-(methylsulfonyloxy)pyridine

At 0° C., initially 7.9 g of triethylamine and then 8.5 g of methanesulfonyl chloride were added to 11.6 g of 2,3-dichloro-5-hydroxypyridine in 150 ml of methylene chloride. The mixture was subsequently stirred at approximately 20° C. for 17 hours and then washed with 100 ml of water. The organic phase was dried over magnesium sulfate and then concentrated. The resulting crude product was purified by silica gel chromatography (mobile phase: ethyl acetate/cyclohexane (1:1)). Yield: 9.1 g.

Intermediate 1.8: 2-Chloro-5-(methylsulfonyloxy)-2-(phenylsulfonyl)pyridine

A mixture of 8.9 g of 2,3-dichloro-5-(methylsulfonyloxy)pyridine, 4.2 g of thiophenol and 20 mg of copper powder was heated at 170° C. for 2 hours and, after cooling to approximately 20° C., admixed dropwise first with a mixture of 50 ml of glacial acetic acid and 20 ml of water and then, with cooling, with a mixture of 157 g of aqueous sodium hypochlorite solution (containing 13% of active chlorine) and 50 ml of water. The mixture was subsequently stirred at approximately 20° C. for 17 hours, and the entire reaction mixture was then stirred into 300 ml of water. The mixture was extracted three times with 200 ml of ethyl acetate each time, and the combined organic phases were then dried over magnesium sulfate and finally concentrated. The crude product was purified by silica gel chromatography (mobile phase: ethyl acetate/cyclohexane (1:1)). Yield: 5.7 g.

Example 2

Compound Ia.363 in Table 1

Initially, a solution of 13.5 g of sodium bicarbonate in 100 ml of water was added dropwise to a mixture of 2,3-dichloro-5-methylsulfonylpyridine, 4-chloro-2-fluoro-5-methoxyboronic acid and 100 ml of tetrahydrofuran, and 1 g of tetrakis(triphenylphosphine)palladium was then added. The mixture was stirred at reflux temperature for 14 hours, after which 150 ml of methyl tert-butyl ether were added to the reaction mixture. The organic phase was subsequently separated off. The aqueous phase was extracted twice with in each case 150 ml of methyl tert-butyl ether. The combined organic phases were then dried over magnesium sulfate and finally concentrated. The crude product was purified by silica gel chromatography (mobile phase: ethyl acetate/cyclohexane (1:1)). Yield: 5.0 g.

Example 3

Compound Ia.362 in Table 1

14.4 ml of a 1 molar solution of boron tribromide in methylene chloride were added dropwise to 4.8 g of 2-(4-chloro-2-fluoro-5-methoxyphenyl)-3-chloro-5-(methylsulfonyl-oxy)pyridine (compound No. Ia.363) in 100 ml of methylene chloride. The mixture was subsequently stirred at approximately 20° C. for 37 hours and then at reflux temperature for 7 hours. 100 ml of ice-water were then added dropwise to the reaction mixture. The phases were separated and the aqueous phase was then extracted twice with in each case 100 ml of methylene chloride. The combined organic phases were finally dried over magnesium sulfate and then concentrated. The crude product was purified by silica gel chromatography (mobile phase: ethyl acetate/cyclohexane (1:1)). Yield 3.2 g.

Example 4

Compound Ia.374 in Table 1

0.3 g of potassium carbonate and 0.25 g of allyl bromide were added successively to 0.6 g of 2-(4-chloro-2-fluoro-5- hydroxyphenyl)-3-chloro-5-(methylsulfonyl-oxy) pyridine (compound No. Ia.362) in 100 ml of dimethylformamide. The reaction mixture was subsequently stirred at approximately 20° C. for 17 hours and then introduced into 300 ml of water. The resulting product of value was extracted with 3 x 150 ml of methyl tert-butyl ether. The combined organic phases were dried over magnesium sulfate and finally concentrated. The crude product was purified by silica gel chromatography (mobile phase: ethyl acetate/cyclohexane (1:1)). Yield: 80 mg.

The physical data of the active compounds I described above and of other compounds according to the invention which were prepared in a similar manner are listed in Table 2 below:

TABLE 2

| No. | $R^5$ | m.p. [° C.] |
|---|---|---|
| Ia.159 | $OCH_2$—CO—$OCH_3$ | oil |
| Ia.169 | $OCH(CH_3)$—CO—$OCH_3$(racemate & R enantiomer) | oil |
| Ia.362 | OH | 132–133 |
| Ia.363 | $OCH_3$ | 118–120 |
| Ia.374 | $OCH_2$—CH=$CH_2$ | oil |
| Ia.381 | $OCH_2$—C≡CH | 110–112 |
| Ia.636 | $OCH(CH_3)$—CO—$OCH_2$—$CH_2$—$OCH_3$ (R enantiomer) | oil |
| Ia.637 | $OCH(CH_3)$—CO—$OCH_2$—CH=$CH_2$ (R enantiomer) | oil |

Use Examples (Herbicidal Activity)

The herbicidal activity of the substituted 2-phenylpyridines I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this has been adversely affected by the active compounds.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The rate of application for the post-emergence treatment was 15.6 and 7.8 g of a.s./ha.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The plants used in the greenhouse experiments were of the following species:

| Scientific name | Common name |
|---|---|
| Abutilon theophrasti | velvet leaf |
| Amaranthus retroflexus | redroot pigweed |
| Chenopodium album | lambsquarters (goosefoot) |
| Ipornoea species | morning glory |
| Polygonum persicaria | redshank |

At application rates of 15.6 and 7.8 g of a.s./ha, the compounds Nos. Ia.169, Ia.381 and Ia.636 (R enantiomer) displayed very good herbicidal activity against the above-mentioned plants.

Use Examples (Desiccant/defoliant Activity)

The test plants used were young cotton plants with four leaves (without cotyledons) which had been grown under greenhouse conditions (relative atmospheric humidity 50 to 70%; day/night temperature 27/20° C.).

The young cotton plants were subjected to foliar treatment to a runoff point with aqueous preparations of the active compounds (with an addition of 0.15% by weight of the fatty alcohol alkoxide Plurafac® LF 700 2), based on the spray mixture). The amount of water applied was 1000 l/ha (converted). After 13 days, the number of leaves shed and the degree of defoliation in % were determined.

No leaves were shed in the untreated control plants.

We claim:

1. A compound of formula I

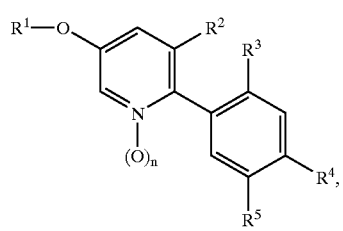

where:

n is zero or 1;

$R^1$ is aminosulfonyl, $C_1$–$C_6$-alkylsulfinyl, $C_1$–$C_6$-alkylsulfonyl or $C_1$–$C_6$-haloalkylsulfonyl;

$R^2$,$R^3$ independently of one another are hydrogen or halogen;

$R^4$ is cyano, hydroxyl, halogen, $C_1$–$C_6$-alkoxy or phenylmethoxy, where the phenyl ring is unsubstituted or carries from one to three substituents, in each case selected from the group consisting of hydroxyl, halogen, $C_1$–$C_6$-alkyl, $C_1$–$C_6$-haloalkyl, $C_1$–$C_6$-alkoxy, $C_1$–$C_6$-haloalkoxy, hydroxycarbonyl, ($C_1$–$C_6$-alkoxy) carbonyl and ($C_1$–$C_6$-alkoxy)carbonyl-$C_1$–$C_6$-alkoxy;

$R^5$ is hydrogen, nitro, cyano, hydroxylamino, halogen, $C_1$–$C_6$-alkyl, $C_1$–$C_6$-haloalkyl, —COCl, —CO—$OR^6$, —CO—N($R^7$)$R^8$, —CO—($C_1$–$C_4$-alkylene)—CO—$OR^6$, —CO—O—($C_1$–$C_4$-alkylene)—CO—N($R^7$)$R^8$, —$X^1$—($C_1$–$C_4$-alkylene)—CO—$R^6$, —$X^1$—($C_1$–$C_4$-alkylene)—CO—$OR^6$, —$X^1$—($C_1$–$C_4$-alkylene)—CO—O—($C_1$–$C_4$-alkylene)—CO—$OR^6$, —$X^1$—($C_1$–$C_4$-alkylene)—CO—N($R^7$)$R^8$, —$X^1$—$R^9$, —CH=C($R^{10}$)—CO—$OR^6$, —CH=C($R^{10}$)—CO—O—($C_1$–$C_4$-alkylene)—CO—$OR^6$, —CH=C($R^{10}$)—CO—N($R^7$)$R^8$, formyl, —CO—$R^6$,

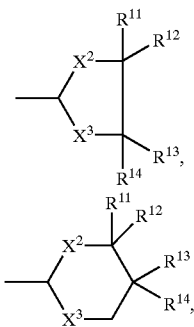

—C(R$^8$)=N—OR$^{15}$, —X$^1$—(C$_1$C$_4$-alkylene)—C(R$^8$)=N—OR$^{15}$, —CH=C(R$^{10}$)—C(R$^8$)=N—OR$^{15}$, —CH(C$_1$–C$_6$-alkoxy)$_2$, —CN(R$^{16}$)R$^{17}$, —N(R$^{16}$)—SO$_2$—(C$_1$–C$_6$-alkyl), —CN(R$^{16}$)—CO—(C$_1$–C$_6$-alkyl), chlorosulfonyl, hydroxysulfonyl or —SO$_2$—N(R$^{18}$)R$^{19}$;

R$^6$ is hydrogen, C$_1$–C$_6$-alkyl, C$_1$–C$_6$-haloalkyl, C$_3$–C$_6$-alkenyl, C$_3$–C$_6$-alkynyl, C$_3$–C$_6$-cycloalkyl or C$_1$–C$_6$-alkoxy-C$_1$–C$_6$-alkyl;

R$^7$ is hydrogen or C$_1$–C$_6$-alkyl;

R$^8$ is hydrogen, hydroxyl, C$_1$–C$_6$-alkyl, hydroxycarbonyl-C$_1$–C$_6$-alkyl, (C$_1$–C$_6$-alkoxy)carbonyl-C$_1$–C$_6$-alkyl, C$_1$–C$_6$-alkoxy, C$_1$–C$_6$-haloalkoxy, phenyl-C$_1$–C$_6$-alkoxy, C$_3$–C$_6$-alkenyloxy or C$_3$–C$_6$-alkynyloxy;

R$^9$ is hydrogen, C$_1$–C$_6$-alkyl, C$_1$–C$_6$-haloalkyl, C$_3$–C$_6$-alkenyl, C$_3$–C$_6$-alkynyl, C$_3$–C$_6$-cycloalkyl or C$_1$–C$_6$-alkoxy-C$_1$–C$_6$-alkyl;

R$^{10}$ is hydrogen, halogen or C$_{1\,6}$-alkyl;

R$^{11}$–R$^{14}$ independently of one another are hydrogen, C$_1$–C$_6$-alkyl or (C$_1$–C$_6$-alkoxy)carbonyl;

R$^{15}$ is hydrogen, C$_1$–C$_6$-alkyl, phenyl-C$_1$–C$_6$-alkyl, (C$_1$–C$_6$-alkoxy)carbonyl-C$_1$–C$_6$-alkyl, C$_3$–C$_6$-alkenyl or C$_3$–C$_6$-alkynyl;

R$^{16}$ is hydrogen or C$_1$–C$_6$-alkyl;

R$^{17}$ is hydrogen, C$_1$–C$_6$-alkyl, hydroxycarbonyl-C$_1$–C$_6$-alkyl, (C$_1$–C$_6$-alkoxy)carbonyl-C$_1$–C$_6$-alkyl or C$_1$–C$_6$-alkoxy;

R$^{18}$ is hydrogen or C$_1$–C$_6$-alkyl;

R$^{19}$ is hydrogen, C$_1$–C$_6$-alkyl, hydroxycarbonyl-C$_1$–C$_6$-alkyl, (C$_1$–C$_6$-alkoxy)carbonyl-C$_1$–C$_6$-alkyl or C$_1$–C$_6$-alkoxy;

X$^1$–X$^3$ independently of one another are oxygen or sulfur; or an agriculturally useful salt of the compound wherein R$^6$=hydrogen.

2. The compound of formula I defined in claim 1 or the salt thereof, where

R$^5$ is hydrogen, nitro, cyano, hydroxylamino, C$_1$–C$_6$-alkyl, C$_1$–C$_6$-haloalkyl, —COCl, —CO—OR$^6$, —CO—O—(C$_1$–C$_4$-alkylene)—CO—OR$^6$, —CO—(C$_1$–C$_4$-alkylene)—CO—OR$^6$, —CO—(C$_1$–C$_4$-alkylene)—CO—O—(C$_1$–C$_4$-alkylene)—CO—OR$^6$, —COR$^9$, formyl, —CH=N—OR$^{15}$ or —CNH$_2$;

R$^6$ is hydrogen, C$_1$–C$_6$-alkyl, C$_3$–C$_6$-alkenyl, C$_3$–C$_6$-alkynyl or C$_1$–C$_6$-alkoxy-C$_1$–C$_6$-alkyl;

R$^9$ is hydrogen, C$_1$–C$_6$-alkyl, C$_3$–C$_6$-alkenyl or C$_3$–C$_6$-alkynyl and R$^{15}$ is C$_1$–C$_6$-alkyl.

3. A herbicidal composition, comprising an effective amount of at least one compound of formula I defined in claim 1 or the salt thereof, and at least one inert liquid or solid carrier and optionally at least one surfactant.

4. A composition for desiccating or defoliating plants, comprising an effective amount of at least one compound of formula I defined in claim 1 or the salt thereof, and at least one inert liquid or solid carrier and optionally at least one surfactant.

5. A process of preparing the composition defined in claim 3, which comprises mixing the effective amount of the at least one compound of formula I or the salt thereof, at least one inert liquid or solid carrier and optionally at least one surfactant.

6. A process of preparing the composition defined in claim 4, which comprises mixing the effective amount of the at least one compound of formula I or the salt thereof, at least one inert liquid or solid carrier and optionally at least one surfactant.

7. A method for controlling undesirable vegetation, which comprises allowing an effective amount of at least one compound of formula I defined in claim 1 or the salt thereof, to act on plants, their habitat or on seeds.

8. A method for desiccating or defoliating plants, which comprises allowing an effective amount of at least one compound of formula I defined in claim 1 or the salt thereof, to act on plants.

9. The process of claim 8, wherein the plants are cotton plants.

10. A compound of formula IIa

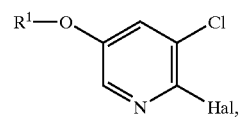

where

Hal is chlorine or bromine, and

R$^1$ is aminosulfonyl, C$_1$–C$_6$-alkylsulfinyl, C$_1$–C$_6$-alkylsulfonyl or C$_1$–C$_6$-haloalkylsulfonyl.

* * * * *